United States Patent [19]

MacWhorter et al.

[11] Patent Number: 5,690,904
[45] Date of Patent: Nov. 25, 1997

[54] DIAGNOSTIC RADIOPHARMACEUTICAL COMPOUNDS (THAT)

[75] Inventors: Susan E. MacWhorter, Belmont; Tiann-long Wu, Emeryville; Douglas S. White, San Francisco, all of Calif.

[73] Assignee: Amersham International plc, Buckinghamshire, United Kingdom

[21] Appl. No.: 430,284

[22] Filed: Apr. 28, 1995

Related U.S. Application Data

[63] Continuation of Ser. No. 89,952, Jul. 12, 1993, abandoned.
[51] Int. Cl.$^6$ ............... A61K 51/04; C07F 13/00
[52] U.S. Cl. .................................. 424/1.65; 534/14
[58] Field of Search .................... 534/14; 424/1.65

[56] References Cited

U.S. PATENT DOCUMENTS

| | | | |
|---|---|---|---|
| 4,638,051 | 1/1987 | Burns et al. | 534/14 |
| 4,746,505 | 5/1988 | Jones et al. | 424/1.1 |
| 4,988,496 | 1/1991 | Srinivasan et al. | 424/1.1 |
| 5,026,913 | 6/1991 | McBride et al. | 564/440 |
| 5,071,636 | 12/1991 | Yamauchi et al. | 424/1.1 |
| 5,080,884 | 1/1992 | McBride et al. | 424/1.1 |
| 5,371,184 | 12/1994 | Rajagopalan et al. | 530/324 |
| 5,382,654 | 1/1995 | Lyle et al. | 530/311 |

FOREIGN PATENT DOCUMENTS

0279417 B1  5/1992  European Pat. Off. .

OTHER PUBLICATIONS

Kung et al., J. Nucl. Med. 25 326–332 (1984).
Kung et al., 9th Int. Symp. Radiopharm. Chem. Paris, France (Apr. 6–10, 1992) Paper A11.
Taylor et al., J. Nucl. Med. 33 1836–1842 (1992).
Bryson et al., Inorg. Chem. 27, 2154–2161 (1988).
Rao et al., Nucl. Med. Biol. 19 (8) 889–895 (1992).

*Primary Examiner*—John Kight
*Assistant Examiner*—Lara C. Kelley
*Attorney, Agent, or Firm*—Wenderoth, Lind & Ponack

[57] ABSTRACT

Tetradentate ligands are used to form neutral 99m-technetium complexes which may be useful as radiopharmaceuticals e.g. as brain imaging agents. The ligands have the structure

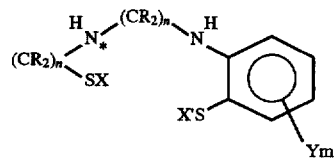

where n is 2 or 3, m is 0–4, R is H or substituted or unsubstituted $C_1$–$C_6$ alkyl, provided that one $CR_2$ group adjacent the starred nitrogen atom represents CO and forms with the adjacent N atom, a —CONH— amide group, Y is unsubstituted or substituted $C_1$–$C_6$ alkyl, and one of X and X' represents H or a labile thiol protecting group while the other is unsubstituted or substituted $C_1$–$C_6$ alkyl, alkenyl or alkynyl.

6 Claims, No Drawings

DIAGNOSTIC RADIOPHARMACEUTICAL COMPOUNDS (THAT)

This application is a continuation of now abandoned application, Ser. No. 08/089,952, filed Jul. 12, 1993, now abandoned

FIELD OF THE INVENTION

The present invention relates to diagnostic radiopharmaceutical compounds and, in particular, ligands useful as intermediates for producing novel $^{99m}$Tc labelled radiodiagnostic agents. Said ligands contain amide, amine, thioether and thiol coordinating groups for complexing the $^{99m}$Tc metal atom, i.e. $N_2S_2$ ligands.

BACKGROUND TO THE INVENTION AND RELEVANT PRIOR ART

Several classes of neutral technetium complexes of $N_2S_2$ ligands are known:

i) Diaminedtthiol

U.S. Pat. No. 4,638,051 discloses that BAT forms a neutral lipophilic Tc(V) monoxo complex which can cross the blood-brain barrier (BBB) but fails to show retention

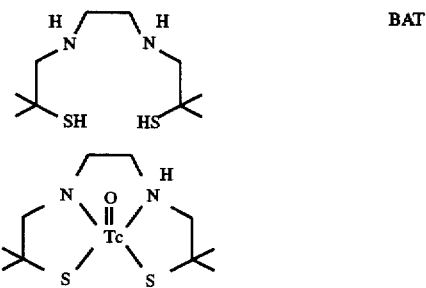

of brain activity[1]. Kung[2] describes the ligand U-BAT which also forms neutral technetium complexes which exhibit brain uptake but no retention.

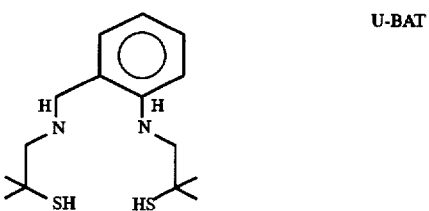

EP 0279417 B1 discloses that the ester-substituted diaminedithiol ligand ECD shows good brain

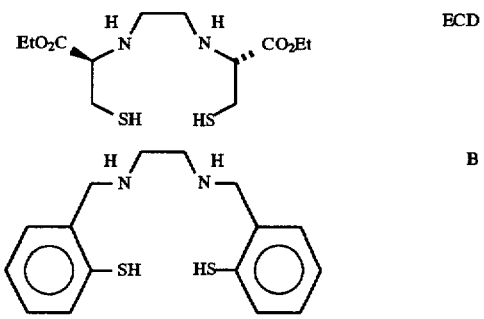

uptake and retention in monkeys. Ester-functionalised diaryl ligands (B) are also claimed.

ii) Diaminetbioetherthiol

U.S. Pat. No. 5,071,636 discloses amine-functionalised BAT ligands, including BAT's in which one of the terminal

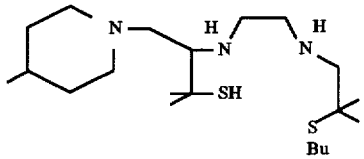

thiols has been alkylated to give a thioether moiety. This ligand system is reported to give a neutral technetium complex which shows brain uptake in rabbits.

U.S. Pat. No. 5,026,913 and U.S. Pat. No. 5,080,884 disclose the PhAT ligand system which forms a neutral technetium complex which shows brain uptake and retention in the monkey[3].

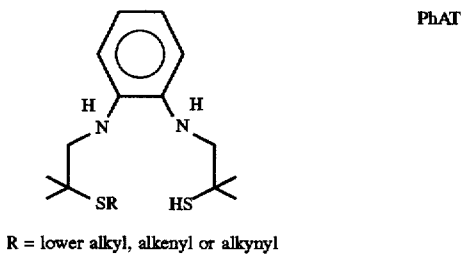

R = lower alkyl, alkenyl or alkynyl iii) Diamidethioetherthiol

Jones and Davison (U.S. Pat. No. 4,746,505) disclosed the S-functionalised $N_2S_2$ ligands shown. They form neutral technetium complexes which are unstable with respect to S-dealkylation regenerating the parent anionic diamidedithiol (DADS) complex[4]. None of the complexes described is useful as a brain agent.

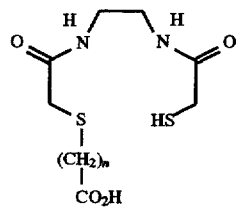

iv) Amideaminedithiol

The technetium complexes of monoaminemonoamide (MAMA) ligands are believed to be neutral[5]. The main thrust of the work was towards bifunctional MAMA ligands for protein/antibody labelling (U.S. Pat. No. 4,988,496).

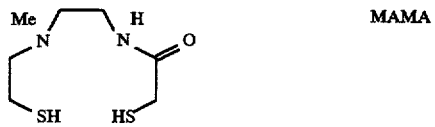

SUMMARY OF THE INVENTION

The invention relates to novel tetradentate ligands (comprising amide, amine, thiol and thioether coordinating groups) which are capable of forming neutral complexes with $^{99m}$Tc. Further, the chelates all contain an aromatic amine with an ortho sulphur atom. The invention also claims the $^{99m}$Tc complexes of the said chelates. The neutral lipophilic complexes formed between the chelate and $^{99m}$Tc are useful as radiopharmaceutical diagnostic agents with particular reference to brain imaging. The ligands claimed are represented by the structure below:

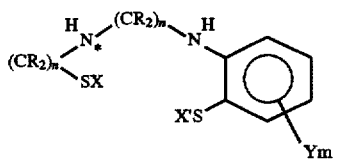

where n is 2 or 3 m is 0 to 4

R is the same or different at different places in the molecule, and each is $C_1$ to $C_6$ alkyl, alkoxyalkyl, aminoalkyl, hydroxyalkyl, or 2 R's of any $CR_2$ group and/or two or more adjacent $CR_2$ groups may be combined to form a $C_3$–$C_6$ cycloalkyl, aryl, heteroaryl, spiropiperidinyl or other saturated or unsaturated heterocyclic ring, with the proviso that one $CR_2$ group adjacent the starred nitrogen atom represents CO and forms, together with the adjacent N atom, a —CONH— amide group, Y is the same or different at different places in the molecule and each is $C_1$–$C_4$ alkyl, alkoxyalkyl, alkoxy, amino, isothiocyanate or acyloxy, one of X and X' is H or a labile thiol protecting group and the other is $C_1$–$C_6$ alkyl, alkenyl, alkynyl, hydroxyalkyl, alkoxyalkyl, aminoalkyl, carboxyalkyl, acyloxyalkyl, aminoalkyl, haloalkyl or nitriloalkyl.

The $^{99m}$Tc complexes claimed are believed to have the structure:

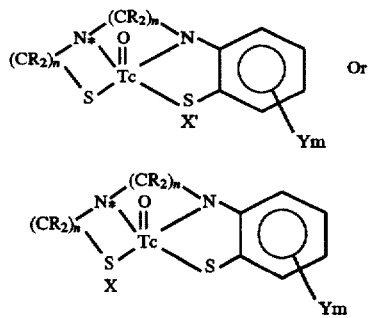

where the symbols are as previously defined. A kit for making the complexes is also claimed.

The labile thiol protecting group may be trityl, benzoyl, tetrahydropyran, benzyl, acetamidomethyl, p-methoxybenzyl, or the corresponding disulphide dimer or others well known in the art.

DETAILED DESCRIPTION OF THE INVENTION

The invention relates to novel tetradentate ligands containing amide, amine, thiol and thioether coordinating groups. They are so designed as to permit the deprotonation of the amide, amine and thiol to provide a trianionic ligand for complexation to a $^{99m}Tc=O^{3+}$ moiety to result in an overall neutral complex. Further, the amine is an aromatic amine so that the acidity of the N-H group has been increased to facilitate the desired deprotonation upon co-ordination required for providing neutral complexes with $^{99m}$Tc. The ortho position of the aromatic amine is substituted by a sulphur atom which can either be a free thiol or thioether. The presence of the aromatic ring provides an increase in lipophilicity which could assist in the ability of the $^{99m}$Tc complexes to cross the blood-brain-barrier.

The ligands can be represented by the structure:

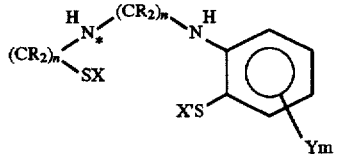

where n, m, R, Y, X and X' are defined as previously.

The following synthetic schemes are illustrative of the means of preparation of the compounds, see Schemes 1–7 and Examples 1–48.

The labelling of the chelates or their salts can be achieved by the addition of generator eluted $NaTcO_4$ to a solution of the chelate or its salt in the presence of a suitable reductant. The reductant is present to reduce the $^{99m}$Tc from its 7 oxidation state to the required 5 oxidation state needed for complexation. Suitable reductants are, for example: dithionite, formamidine sulphonic acid, tin metal and stannous salts, SnII has proved to be particularly suitable.

The thiol group of the chelate can be a free or protected thiol (see Examples 58 60, 62–63) the protecting group being lost under the labelling conditions. After labelling, and if required, the resultant $^{99m}$Tc chelate complexes can be purified by passing through a C-18 Sep Pak column. In this way complexes with a radiochemical purity of >95% can be achieved, the radiochemical purity being verified by both ITLC methods and HPLC. The neutral charge on the complex is confirmed by electrophoresis.

The biodistribution properties of the $^{99m}$Tc complexes produced were studied in rats (see Example 64). The complexes showed good brain uptake confirming their neutral character and thus ability to cross the blood-brain-barrier. Further, there was retention of the complexes in the brain as shown by biodistribution studies at different time points, see Table 1.

The invention will be further illustrated by the following examples. It is obvious to those skilled in the art that the examples provided are not limiting but merely illustrative of the scope of the invention.

Scheme 1:
Synthesis of T711 (Examples 1–8)

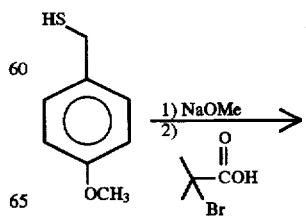

Scheme 1:
Synthesis of T711 (Examples 1–8)
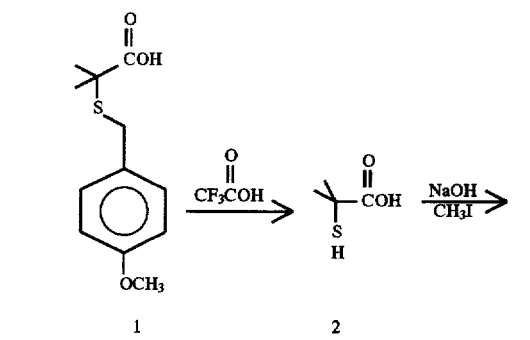
1
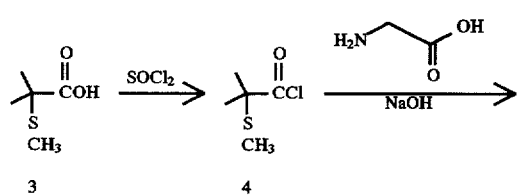
3   4
5
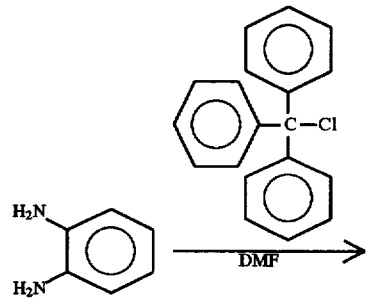
6
Scheme 1:
Synthesis of T711 (Examples 1–8)
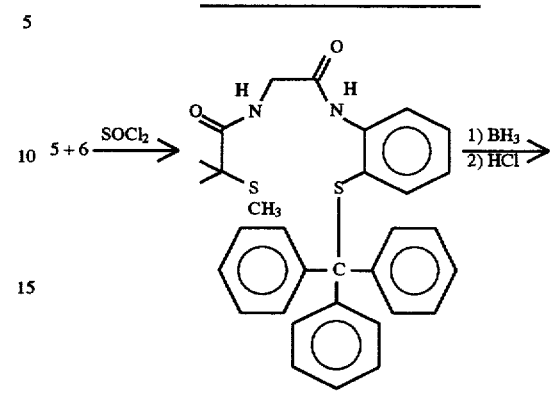
7
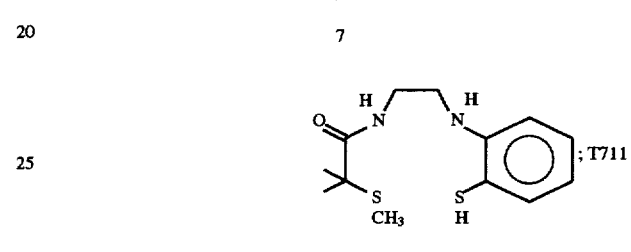
8 ; T711
Scheme 2:
Synthesis of T712 (Examples 9–11)
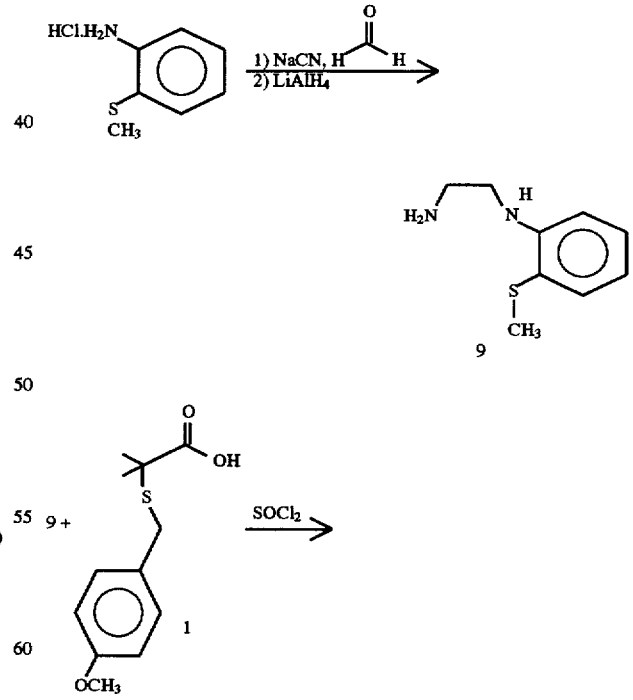
9
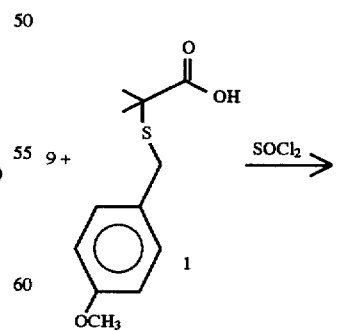
1

Scheme 2:
Synthesis of T712 (Examples 9–11)
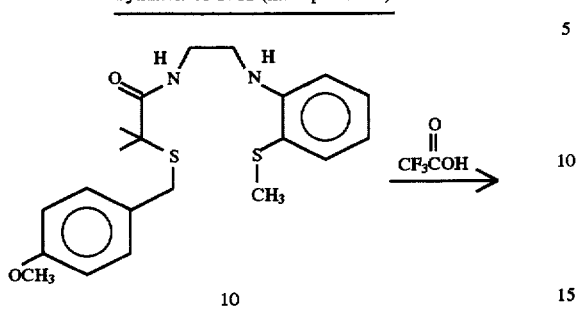
Scheme 3:
Synthesis of T713, T714 and T715 (Examples 12–23)
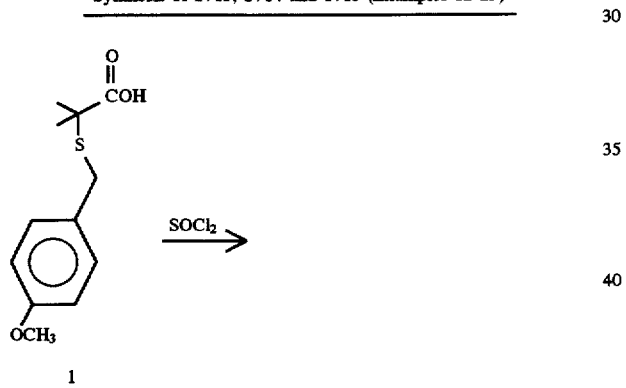
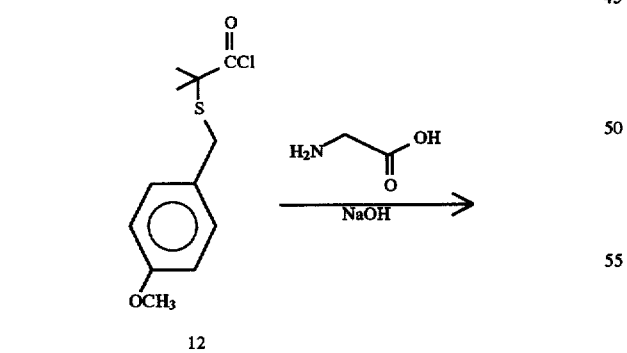
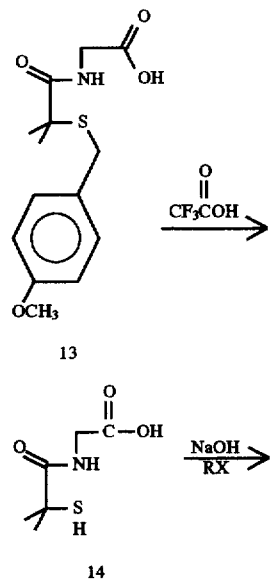
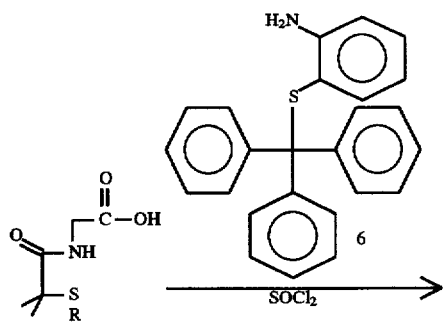
15: R = CH$_2$CH$_2$CH$_3$
18: R = CH$_2$CH$_2$CH$_2$CH$_3$
21: R = CH$_2$CH$_3$
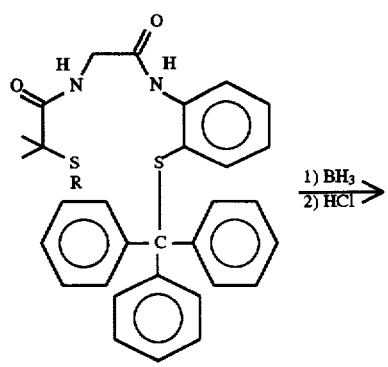
16: R = CH$_2$CH$_2$CH$_3$
19: R = CH$_2$CH$_2$CH$_2$CH$_3$
22: R = CH$_2$CH$_3$

9
-continued
Scheme 3:
Synthesis of T713, T714 and T715 (Examples 12–23)
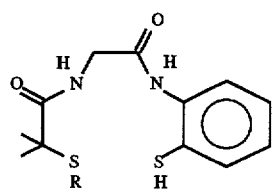
T713; 17: R = CH₂CH₂CH₃
T714; 20: R = CH₂CH₂CH₂CH₃
T715; 23: R = CH₂CH₃
Scheme 4:
Synthesis of T717 (Examples 24–7)
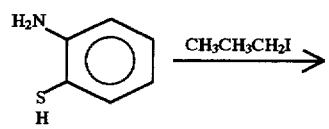
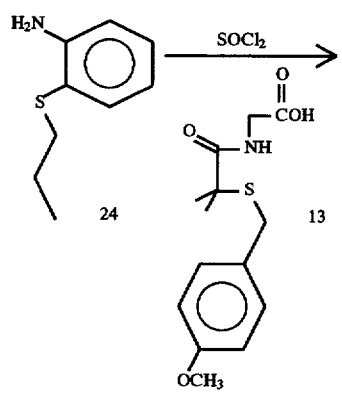
24
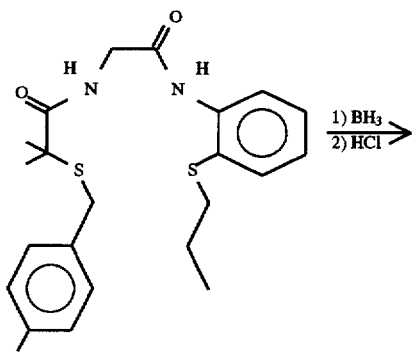
25
10
-continued
Scheme 4:
Synthesis of T717 (Examples 24–7)
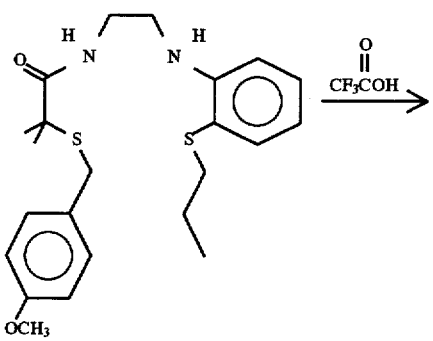
26
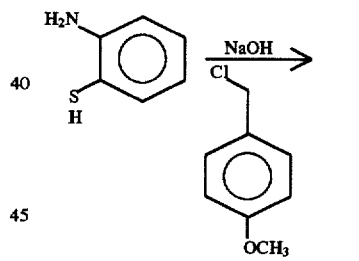
; T717
27
Scheme 5:
Synthesis of T719, T721 and T722 (Examples 28–36)
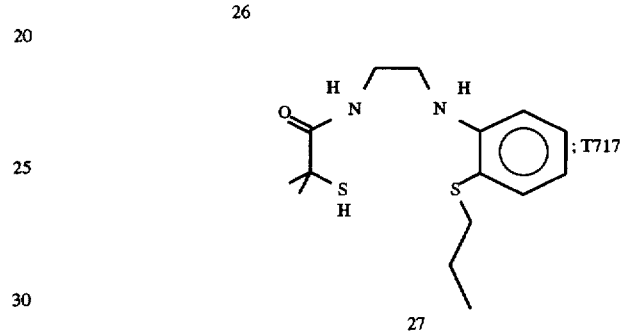
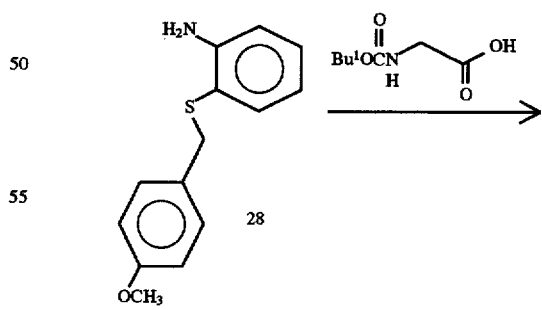
28

-continued
Scheme 5:
Synthesis of T719, T721 and T722 (Examples 28-36)
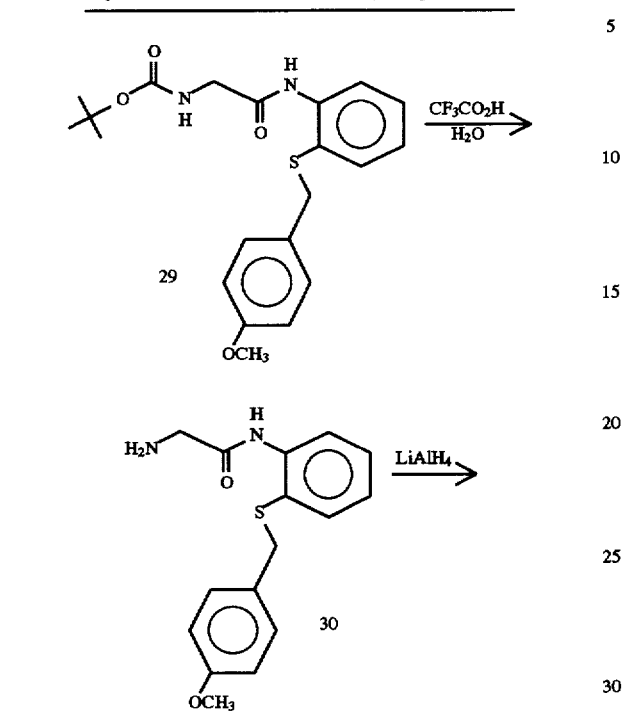
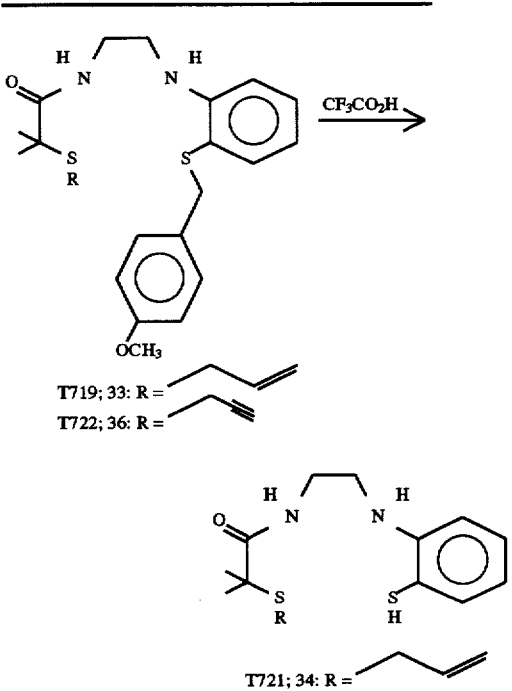
Scheme 6:
Synthesis of T726, T727, T728, T730 and T731 (Examples 37-41 and 47-8)
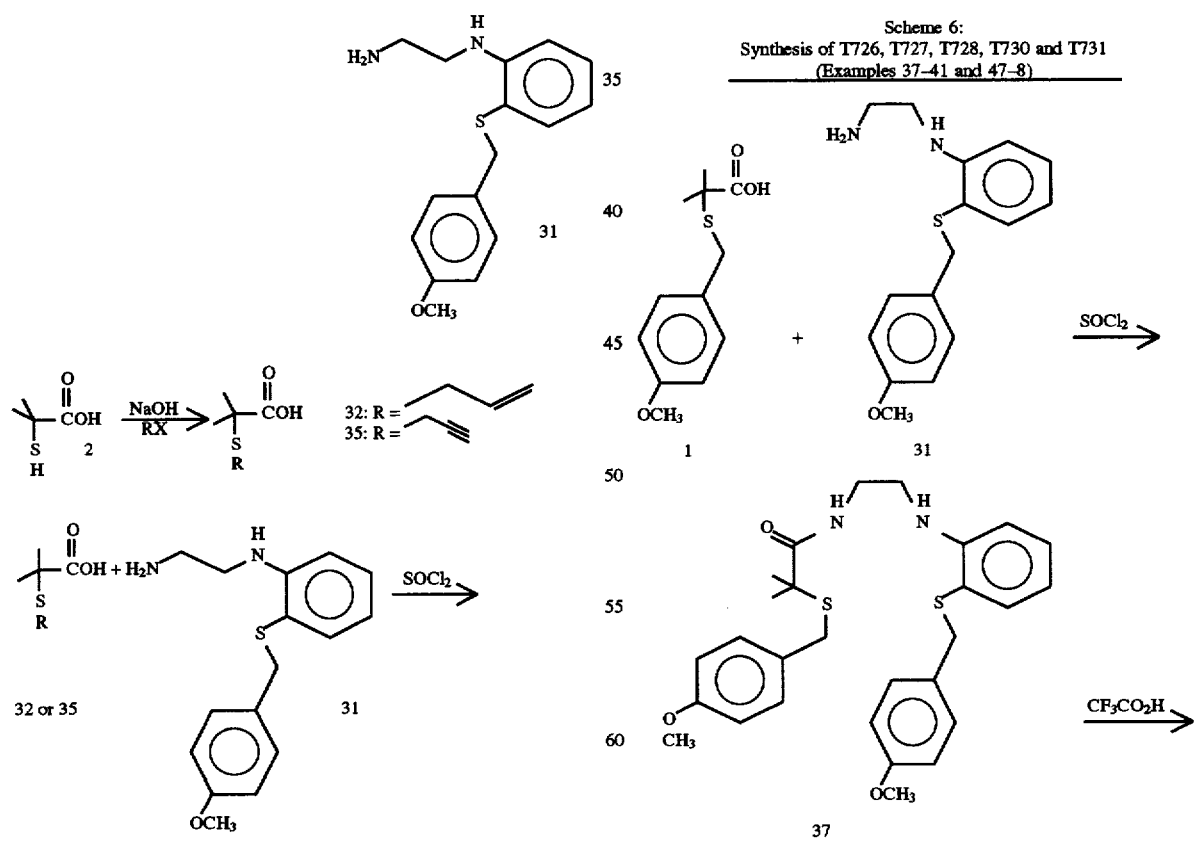

Scheme 6:
Synthesis of T726, T727, T728, T730 and T731
(Examples 37-41 and 47-8)
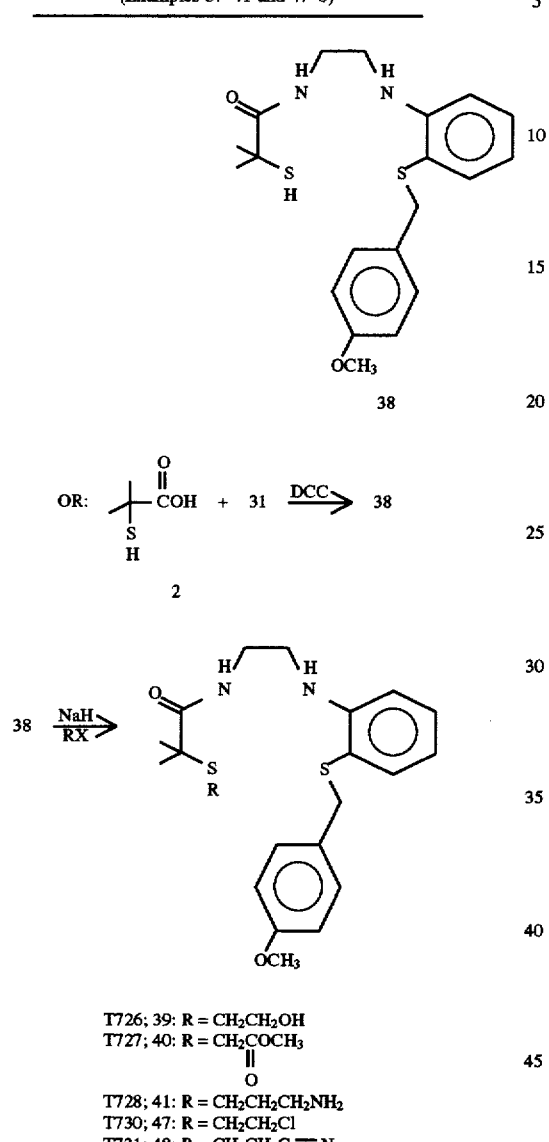
T726; 39: R = CH$_2$CH$_2$OH
T727; 40: R = CH$_2$COCH$_3$
              ‖
              O
T728; 41: R = CH$_2$CH$_2$CH$_2$NH$_2$
T730; 47: R = CH$_2$CH$_2$Cl
T731; 48: R = CH$_2$CH$_2$C≡N
Scheme 7:
Synthesis of T729 (Example 42-6)
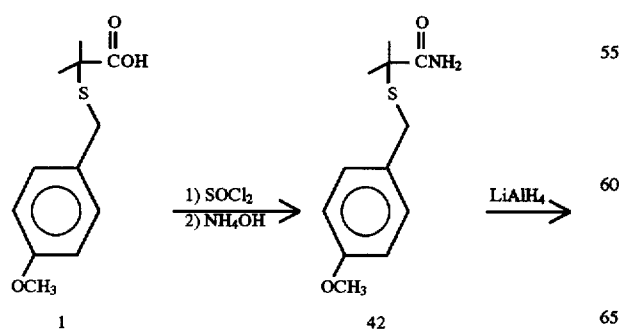
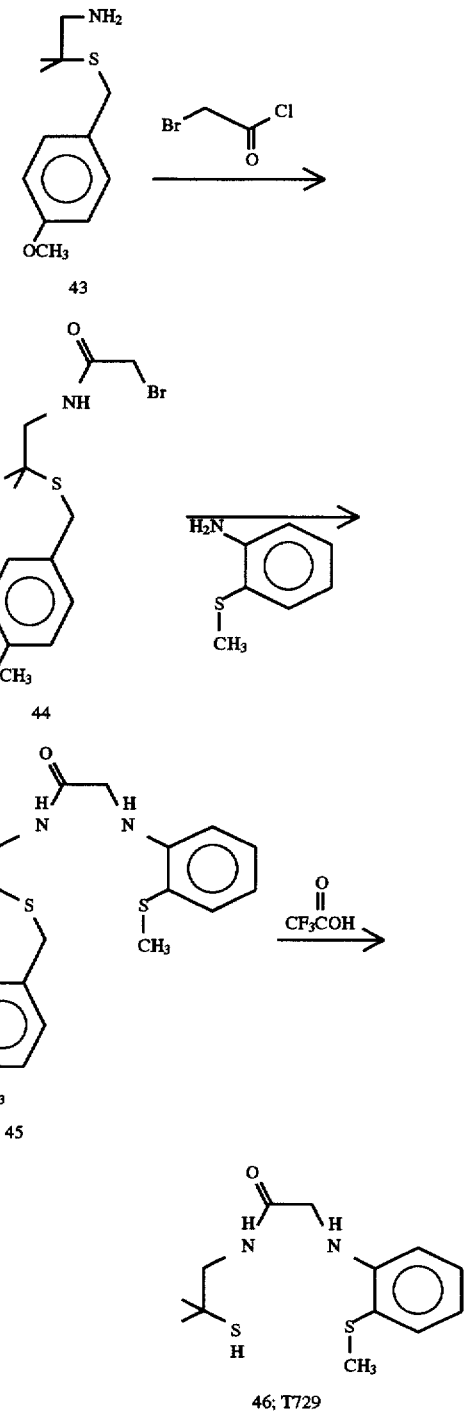
EXPERIMENTAL
EXAMPLE 1
2-(4-Methoxybenzylthio)-2-methylpropionic acid
Sodium methoxide (81 g, 1.5 mol) was added to 50 ml methanol and 375 ml freshly distilled tetrahydrofuran. The slurry was stirred in an ice bath and 4-methoxybenzylmercaptan (80 g, 0.52 mol) was added slowly. The cloudy orange solution was stirred at room temperature for 1.25 hours, 2-bromo-2-methylproprionic acid (83.5 g, 0.5 mol) was dissolved in 200 ml tetrahydrofuran and added to the mixture. The thick slurry was stirred at reflux for 70 h, then cooled to room temperature. Iodine crystals were added until a red colour persisted. The mixture was dissolved in 2000 ml 0.5M sodium hydroxide solution, and washed with 2×1000 ml ether. The aqueous layer was acidified and extracted with 2×1000 ml ether. The ether layer was washed with 2×1000 ml saturated sodium chloride solution, dried over sodium sulphate, and filtered. The solvent was removed by rotary evaporation to yield an orange solid. This was recrystallised from ethyl acetate to give 70.3 g of the desired product (59% yield) as white crystals. $^1$H NMR (60 MHz, CDCl$_3$): 1.57 (s, 6H), 3.73 (s, 3H), 3.83 (s, 2H), 6.5–7.5 (m, 4H), 10.90 (brs, 1H) ppm. TLC (50% ether/hexane) R$_f$ 0.30.

EXAMPLE 2

2-Mercapto-2-methylpropionic acid

The carboxylic acid prepared in Example 1 (5.68 g, 23.7 mmol) was dissolved in 40 ml trifluoroacetic acid and stirred at reflux under nitrogen for 30 minutes. The solution was cooled to 0° C. and 10 ml of a 50% mixture of triethylsilane in trifluoroacetic acid was added dropwise. The mixture was warmed to reflux, and stirred for an additional 30 minutes. The volatile material was removed by rotary evaporation and the residue was dissolved in dichloromethane and washed with 3×100 ml 2M sodium hydroxide solution. The aqueous layers were combined and brought to pH 4.0 with 1M hydrochloric acid. The aqueous layer was extracted with 6×100 ml ethyl acetate. The organic layers were combined, dried over anhydrous sodium sulphate, and the solvent was removed by rotary evaporation to give 2.05 g of the desired product as a white solid (72% yield). $^1$H NMR (60 MHz, CDCl$_3$): 1.60 (s, 6H), 2.50 (brs, 1H), 9.23 (s, 1H) ppm. TLC (ethyl acetate) R$_f$ 0.84.

EXAMPLE 3

2-Methylthio)-2-methylpropionic acid

A Sodium thiomethoxide (15.40 g, 220 mmol) was reacted with 34.86 g 2-bromo-2-methylpropionic acid (208 mmol) in 400 ml tetrahydrofuran by the method described in Example 1. This gave 22.80 g of the desired product as a yellow liquid, 50% pure by NMR. $^1$H NMR (60 MHz, CDCl$_3$): 1.50 (s, 6H), 1.60 (s, 6H), 1.97 (s, 3H), 2.14 (s, 3H) ppm.
B Alternatively, the mercaptan prepared in Example 2 (3.30 g, 27.5 mmol) was dissolved in 75 ml ethanol and treated with 3.1 g sodium hydroxide (78 mmol) dissolved in 25 ml water. The mixture was stirred at room temperature for 20 minutes. Methyl iodide (2.4 ml, 38 mmol) was added and the mixture continued stirring for 1 hour. The volatile material was removed by rotary evaporation and the residue was dissolved in a mixture of ether and 2M sodium hydroxide solution. The mixture was extracted with 3×250 ml 2M sodium hydroxide solution. The aqueous layer was brought to pH 2.0 with dilute hydrochloric acid and extracted with 3×100 ml ethyl acetate. The organic layers were combined, dried over anhydrous sodium sulphate, and the solvent was removed by rotary evaporation to give 2.78 g of the desired product as a yellow oil (75% yield). 1H NMR (60 MHz, CDCl$_3$): 1.50 (s, 6H), 2.14 (s, 3H), 9.90 (s, H) ppm. TLC (50% ethyl acetate/hexane) R$_f$ 0.66.

EXAMPLE 4

2-Methyl-2-(methylthio)propanoyl chloride

The carboxylic acid prepared in Example 3A (7.20 g, 0.054 mol) was dissolved in 100 ml dichloromethane. Thionyl chloride (4.73 ml, 0.065 mol) was added dropwise, and the mixture was stirred at room temperature for 1 hour, and at reflux for 1.5 hours. The solution was cooled an the solvent was removed by rotary evaporation. The crude yellow oil was purified by fractional distillation (56° C.; water aspirator) to give 10.69 g of a yellow liquid (19% yield). 1H NMR (60 MHz, CDCl$_3$): 1.58 (s, 6H), 2.06 (s, 3H) ppm.

EXAMPLE 5

2-N-[2-methyl-2-(methylthio)-1-oxopropyl] aminoacetic acid

In a 1000 ml 3-necked flask equipped with two addition funnels was added 4.78 g glycine (0.062 mol) dissolved in 40 ml 2M sodium hydroxide solution. The acyl halide prepared in Example 4 (10.50 g, 0.067 mol) was placed in one of the addition funnels and 10 ml of 0.01M sodium hydroxide solution was placed in the other. The reagents were added simultaneously at 0° C., and at such rates that the solution was always slightly alkaline. The mixture was then stirred at room temperature for 1 hour. The solution was acidified with concentrated hydrochloric acid, and extracted with 3×100 ml ether. The combined ether layers were washed with 2×50 ml saturated sodium chloride solution, and dried over anhydrous sodium sulphate. Removal of solvent by rotary evaporation gave a white solid which 5 was recrystallised from ethyl acetate and petroleum ether to give 9.52 g of the desired product as white crystals (73% yield). mp 62°–64° C. 1H NMR (60 MHz, CDCl$_3$): 1.50 (s, 6H, CCH$_3$) 2.06 (s, 3H, SCH$_3$), 4.04 (d, J=6 Hz, 2H, NCH$_2$), 7.69 (bt, 1H, CONH), 10.48 (s, 1H, COOH) ppm.

EXAMPLE 6

2-(Triphenylmethylthio)aniline

To a solution of 3.57 g 2-aminothiophenol (28.6 mmol) in dimethylformamide was added 8.27 g triphenylmethylchloride (29.7 mmol) and the mixture was stirred at room temperature under nitrogen for 70 hours. The mixture was treated with water and extracted three times with ethyl acetate. The organic layers were combined and filtered through a Buchner funnel. The filtrate was washed five times with saturated sodium chloride solution, and dried over anhydrous sodium sulphate. The solvent was removed by rotary evaporation, and the crude product was purified by radial chromatography (gradient, hexane to 10% ethyl acetate/hexane) to give 5.88 g cream coloured solid (56% yield). mp 157°–160° C. TLC (25% EtOAc/hexane) R$_f$ 0.74. $^1$H NMR (400 MHz, CDCl$_3$): 3.36 (brs, 2H, NH$_2$), 6.39 (t, J=7.5Hz, 1H, ArH), 6.45 (d, J=8.4Hz, 1H, ArH), 6.8–7.05 (m, 2H, ArH), 7.1–7.5 (m, 15H, ArH) ppm. $^{13}$C NMR (100 MHz, CDCl$_3$) 43.0, 115.1, 116.2, 117.9, 126.7, 128.3, 129.9, 130.7, 137.8, 144.4 pm.

EXAMPLE 7

N[2-(((2-methyl-2-(methylthio))propionyl)amino) acetyl]-2-(triphenylmethylthio)aniline The carboxylic acid prepared in Example 5 (1.18 g, 6.18 mmol) was suspended in 60 ml benzene (freshly distilled from calcium hydride). Thionyl chloride (0.50 ml, 6.9 mmol) was added dropwise at room temperature. The mixture was heated at reflux for 45 minutes, during which time the solution became homogeneous. The solution was cooled to room temperature, and the aniline prepared in Example 6 (2.91 g, 7.93 mmol) was added. Triethylamine (1 ml, 10 mmol) was added, and the mixture was heated at reflux for 0.5 hours. After cooling to room temperature, ethyl acetate (50 ml) was added and the solution was washed with 2×50 ml 0.5M hydrochloric acid, 2×50 ml 0.5M sodium hydroxide solution and 50 ml saturated sodium chloride solution. The organic layer was dried over anhydrous sodium sulphate. Removal of the solvent by rotary evaporation gave a crude orange oil. This was purified by column chromatography (gradient from hexane to 50% ethylacetate/hexane). The solvent was removed by rotary evaporation to give 2.32 g of a yellow solid (69% yield). mp 140°–142° C. TLC (20% EtOAc/hexane) $R_f$ 0.15. $^1$H NMR (400 MHz, CDCl$_3$): 1.53 (s, 6H, CCH$_3$), 2.09 (s, 3H, SCH$_3$), 3.64 (d, J=5.2 Hz, 2H, NCH$_2$), 6.82 (td, J=7.6, 1.4 Hz, 1H, ArH), 7.15–7.35 (m, 17H, ArH), 7.43 (brt, 1H, CONH), 8.00 (brs, 1H, ArNHCO), 8.21 (d, J=7.7 Hz, 1H, ArH). ppm. $^{13}$C NMR (100 MHz, CDCl$_3$): 12.9, 26.3, 43.7, 49.2, 71.7, 119.5, 120.2, 123.6, 127.2, 127.9, 129.6, 131.2, 137.6, 141.7, 143.5, 166.0, 174.7, ppm.

EXAMPLE 8

N[2-(((2-Methyl-2-(methylthio))propionyl) amino) ethyl]-2-amino thiophenol

The diamide prepared in Example 7 (400 mg, 0.74 mmol) was dissolved in 7 ml tetrahydrofuran and added dropwise to 2.0 ml of 1.0M borane-tetrahydrofuran complex at 0° C. under nitrogen. Half of the mixture was stirred at room temperature for 20 hours. The mixture was treated with 20 ml 1M hydrochloric acid at 0° C., and was stirred for 30 minutes at room temperature. The mixture was extracted three times with ether. The organic layers were combined, washed with saturated sodium chloride solution, and dried over anhydrous sodium sulphate. The solvent was removed by rotary evaporation to give a yellow oil which was purified by radial chromatography (gradient from hexane to 100% ethyl acetate) to give 20mg of the desired product as a yellow oil (19% yield). TLC (50% EtOAc/hexane) $R_f$IR (neat): 3350, 1650 cm$^{-1}$. $^1$H NMR (400 MHz, CDCl$_3$): 1.50 (s, 6H, CCH$_3$), 2.01 (s, 3H, SCH$_3$), 3.29 (m, 2H, NCH$_2$), 3.43 (m, 2H, NCH$_2$), 5.10 (brs, 1H, ArNh), 6.53 (td, J=7.7, 1.2 Hz, 1H, ArH), (dd, J=7.7, 1.1 Hz. 1H, ArH), 7.12 (dd, J=7.6, 1.6 Hz, 1H, ArH), 7.2–7.4 (m, 2H, Arh, CONH) ppm. Mass spectrum m/z 284 (M$^+$), 236 (M$^+$-CH$_3$SH).

EXAMPLE 9

1-Amino-2-N-[2-(methylthio)phenyl]aminoethane 2-(Methylmercapto)aniline was dissolved in ether and hydrogen chloride gas was bubbled into the solution at 0° C. The solid was collected by suction filtration and dried under vacuum. To a solution of 30.61 g 2-(methylmercapto)aniline hydrochloride (175 mmol) dissolved in 152 ml water was added 8.51 g sodium cyanide (173 mmol). A solution of 13.28 g aqueous formaldehyde (37% by weight, 164 mmol) and 109 ml methanol was added and the mixture was stirred under nitrogen at room temperature for 16 hours. The mixture was extracted with 3×200 ml dichloromethane. The organic layers were combined and dried over anhydrous sodium sulphate. The solvent was removed by rotary evaporation to give 29.10 g of the intermediate nitrile, N-[2-S-(methylthio)phenyl] aminoacetonitrile, approximately 90% pure by NMR.

The crude nitrile (27.57 g, 155 mmol) was dissolved in 60 ml ether and added dropwise to a suspension of 7.37 g lithium aluminium hydride (194 mmol) in 90 ml ether at 0° C. The mixture was warmed to room temperature and was stirred under nitrogen for 18 hours. The reaction was cooled to 0° C. and water was added slowly. The mixture was filtered through Celite and washed with ethyl acetate. The filtrate was washed with saturated sodium chloride solution, and dried over anhydrous sodium sulphate. The solvent was removed by rotary evaporation to yield 22.90 g of a brown oil. The brown oil was purified by filtering through a bed of silica gel (elution with ethyl acetate/methanol/water 15M ammonium hydroxide (86:10:3:1) to give 11.8 g of the desired product as a yellow oil (40% yield). $^1$H NMR (60 MHz, CDCl$_3$): 1.36 (brs, 2H), 2.33 (s, 3H), 2.6–3.5 (m, 4H), 5.18 (brs, 1H), 6.3–7.6 (m, 4H) ppm. TLC (86% ethyl acetate/10% methanol/3% water/1% 15M ammonium hydroxide) $R_f$ 0.21.

EXAMPLE 10

N[2-(((2-methyl-2-(4-methoxybenzylthio)) propionyl) amino)ethyl]-2-methylthioaniline The amine prepared in Example 9 (2.30 g, 12.4 mmol) was reacted with the carboxylic acid prepared in Example 1 (2.32 g, 9.67 mmol) and 0.83 ml thionyl chloride (11.4 mmol) by the method described in Example 7. The crude red oil was purified by column chromatography (gradient from hexane to 30% ethyl acetate/hexane). The solvent was removed by rotary evaporation to give 3.15 g of the desired product as an orange oil (81% yield). TLC (30% ethyl acetate/hexane) $R_f$ 0.26. IR (neat): 3370 1685 cm$^{-1}$. $^1$H NMR (400 MHz CDCl$_3$): 1.55 (s, 6H, CCH$_3$), 2.28 (s, 3H, SCH$_3$), 3.30 (m, 2H, NCH$_2$), 3.45 (m, 2H, NCH$_2$), 3.67 (s, 2H, SCH$_2$), 3.75 (s, 3H, OCH$_3$), 5.07 (s, 1H, ArNH), 6.4–7.5 (m, 9H, ArH, CONH) ppm. $^{13}$C NMR (100 MHz, CDCl$_3$: 18.0, 26.9, 34.1, 39.2, 43.5, 50.3, 55.2, 110.0, 114.0, 117.4, 120.2, 129.0, 129.4, 129.9, 133.9, 147.8, 158.7, 175.0 ppm. Mass spectrum m/z 404 (M+), 252 (M$^+$-C$_6$H$_4$SCH$_3$NHCH$_2$).

EXAMPLE 11

N[2-(((2-methyl-2-mercapto)propionyl) amino) ethyl]-2-methylthioaniline

A solution of 2.45 g of the amide prepared in Example 10 (6.06 mmol)in 12 ml trifluoroacetic acid, was stirred at reflux under nitrogen for 30 minutes. The solution was cooled to 0° C. and 6 ml of a 50% mixture of triethylsilane in trifluoroacetic acid was added dropwise. The mixture was warmed to reflux, and stirred an additional 30 minutes. The volatile material was removed by rotary evaporation and the residue was dissolved in dichloromethane and washed with saturated sodium chloride solution. The organic layer was dried over anhydrous sodium sulphate, and the solvent was removed by rotary evaporation to give a yellow oil. The oil was purified by radial chromatography (gradient from hexane to 50% ethyl acetate/hexane) to give 1.6 g of the desired product as a clear oil (93% yield). TLC (30% EtOAc/hexane) $R_f$ 0.37. IR (neat): 3370, 2560, 1650 cm$^{-1}$. $^1$HNMR (400 MHz, CDCl$_3$): 1.60 (s, 6H, CCH$_3$, 2.14 (s, 1H, SH), 2.32 (s, 3H, SCH$_3$), 3.39 (m, 2H, NCH$_2$), 3.52 (m, 2H, NCH$_2$) 5.11 (brs, 1H, ArNH), 6.6–6.8 (m, 2H, ArH), 7.19 (td, J=8.0, 1.7 Hz, 1H, ArH), 7.23 (m, 1H, CONH), 7.40 (dd, J=7.8, 1.6 Hz, 1H, ArH) ppm. $^{13}$C NMR (100 MHz, CDCl$_3$): 18.1, 30.4, 39.5, 43.2, 47.8, 110.1, 117.4, 120.2, 129.4, 134.1, 147.8, 175.6 ppm. Mass spectrum m/z 284 (M+), 252 (M$^+$-S), 250 (M$^+$-H$_2$S), 205 (252-CH$_3$S), 209 (M$^+$-C$_3$H$_7$S).

EXAMPLE 12

2-(4-Methoxybenzylthio)-2-methylpropanoyl chloride

The carboxylic acid prepared in Example 1 (20.00 g, 83.2 mmol) was dissolved in 150 ml dichloromethane and cooled in an ice bath. Thionyl chloride (8.5 ml, 0.12 mol) was added slowly by an addition funnel. The solution was stirred at reflux under nitrogen for 3 hours. The solvent was removed by rotary evaporation to give 24.21 g of the desired product as an orange oil (99% yield). $^1$HNMR (60 MHz, CDCl$_3$): 1.60 (s, 6H), 3.70 (s, 2H), 3.73 (s, 3H), 6.5–7.5 (m, 4H) ppm.

EXAMPLE 13

2-N-[2-S-(4-ethoxybenzylthio)-2-methyl-1-oxopropyl]aminoacetic acid

In a 1000 ml 3-necked flask equipped with two addition funnels was added 8.27 g glycine (0.10 mol) dissolved in 60 ml 2M sodium hydroxide solution. The acyl halide (30.02 g, 0.116 mol) prepared in Example 12 was placed in one of the addition funnels and 20 ml of 0.01M sodium hydroxide solution was placed in the other. The reagents were added separately at 0° C. at such rates that the solution was always only slightly alkaline. The mixture was then stirred at room temperature for 1 hour. The solution was acidified with concentrated hydrochloric acid, and extracted with 3×100 ml ether. The combined ether layers were washed with 2×50 ml saturated sodium chloride solution, and dried over anhydrous sodium sulphate. Removal of solvent of rotary evaporation gave a white solid which was recrystallised from ethyl acetate and petroleum ether to give 30.83 g of the desired product as white crystals (75% yield). mp 101°–102° C. TLC (50% Et$_2$O/hexane) R$_f$ 0.21. $^1$H NMR (60 MHz, CDCl$_3$): 1.53 (s, 6H, CCH$_3$), 3.73 (s, 5H, OCH$_3$ and SCH$_2$), 4.00 (d, J=6 Hz, 2H, NCH$_2$), 6.5–7.4 (m, 4H, aromaticH), 7.60 (brt, J=6 Hz, 1H, NH), 10.03 (s, 1H, COOH) ppm.

EXAMPLE 14

2-N-[mercapto-2-methyl-1-oxopropyl]aminoacetic acid

The carboxylic acid prepared in Example 13 (3.75 g, 12.0 mmol) was reacted with trifluoroacetic acid and triethylsilane by the method described in Example 11. After the volatile material was removed by rotary evaporation the residue was treated with water and washed three times with dichloromethane. The aqueous layer was extracted three times with ethyl acetate. The ethyl acetate layers were combined, dried over anhydrous sodium sulphate, and the solvent was removed by rotary evaporation to give 2.0 g of the desired product as a white solid (94%). TLC (EtOAc) R$_f$ 0.43. $^1$H NMR (60 MHz, CDCl$_3$): 1.60 (s, 6H, CCH$_3$) 2.27 (brs, 1H, SH), 4.07 (d, J=5 Hz, 1H, NCH$_2$), 10.50 (s, 1H, COOH) ppm.

EXAMPLE 15

2-N-[2-Methyl-2-S-(propylthio)-1-oxopropyl]aminoacetic acid

To a solution of the mercaptan prepared in Example 14 (2.0 g, 11 mmol) in 76 ml ethanol, was added 1.7 g sodium hydroxide (42 mmol) in 11 ml water. The mixture was stirred at room temperature for 20 minutes. Propyl iodide (1.70 ml, 17.4 mmol) was added and the mixture stirred an additional hour. The volatile material was removed by rotary evaporation and 2M sodium hydroxide solution and ether were added to the residue. The aqueous layer was separated and brought to pH 2.0 with dilute hydrochloric acid. The aqueous layer was then extracted three times with ethyl acetate. The organic layers were combined and dried over anhydrous sodium sulphate. Removal of the solvent by rotary evaporation gave 2.09 g of the desired product as a clear oil (84% yield). TLC (EtOAc) R$_f$ 0.19. IR (neat): 3360, 1730, 1650 cm$^{-1}$. $^1$H NMR (400 MHz, CDCl$_3$): 0.98 (t, J=7.4 Hz, 3H, CH$_2$Ch$_3$), 1.52 (s, 6H, CCH$_3$), 1.5–1.7 (m, 2H, CH$_2$CH$_3$), 2.53 (t, J=7.4 Hz, 2H, SCH$_2$CH$_2$), 4.08 (d, J=5.6 Hz, 2H, NCH$_2$), 7.73 (brt, J=5.5 Hz, 1H, CONH), 9.15 (brs, 1H, COOH) ppm. $^{13}$C (100 MHz, CDCl$_3$): 13.6, 22.6, 26.8, 31.9, 41.7, 49.7, 173.7, 176.5 ppm. Mass spectrum m/z 219 (M$^+$), 173 (M$^+$-H$_2$O-CO), 145 (M$^+$-NHCH$_2$CO$_2$H).

EXAMPLE 16

N[2-(((2-methyl-2-propylthio)propionyl)amino) acetyl]-2-(triphenylmethylthio)aniline The carboxylic acid prepared in Example 15 (1.54 g, 7.03 mmol) was reacted with 0.6 ml thionyl chloride (8 mmol) and 2.5 g of the aniline, prepared in Example 6, (6.9 mmol) by the method described in Example 7. Triethylamine (1 ml, 10 mmol) wad added after the addition of the aniline. The crude product was purified by column chromatography (gradient from hexane to 20% ethyl acetate/hexane) to give 1.49 g of the desired product as a red solid (38% yield). TLC 30% EtOAc/hexane) R$_f$ 0.59. $^1$H NMR (400 MHz, CDCl$_3$): 0.96 (t, J=7.4 Hz, 3H, CH$_2$CH$_2$), 1.52 (s, 6H, CCH$_3$), 1.0–1.7 (m, 2H, CH$_2$CH$_3$), 2.51 (t, J=7.5 Hz, 2H, SCH$_2$), 3.63 (d, J=5.2 Hz, 2H, NCH$_2$), 6.80 (td, J=7.6 Hz, 1.3 Hz, 1H, arH), 7.1–7.4 (m, 17H, ArH), 7.45 (brt, 5.3 Hz, 1H, CONH), 8.04 (brs, 1H, ArNHCO), 8.22 (d, J=8.1 Hz, 1H, arH) ppm. $^{13}$C NMR (100 MHz, CDCl$_3$): 13.7, 22.7, 26.9, 32.0, 43.8, 49.4, 71.7, 119.5, 120.2, 123.5, 127.1, 127.8, 129.6, 131.2, 137.6, 141.7, 143.5, 165.9, 175.3 ppm. Mass spectrum m/z 326 (M$^+$-C(C$_6$H$_5$)$_3$, 202 (M$^+$-HNC$_6$H$_4$SC (C$_6$H$_5$)$_3$).

EXAMPLE 17

N[2-(((2-methyl-2-propylthio)propionyl)amino)ethyl]-2-aminothiophenol

The diamide prepared in Example 16 (1.28 g, 2.25 mmol) was dissolved in 21 ml tetrahydrofuran. Borane-tetrahydrofuran complex (1.0M, 6.1 ml, 6.1 mmol) was added to this solution, dropwise at 0° C. The mixture was stirred at room temperature under nitrogen, for 16 hours. Dilute hydrochloric acid (60 ml) was added at 0° C., and the mixture was stirred an additional 45 minutes at room temperature. The mixture was extracted three times with ether. The organic layers were combined, washed with 0.5M sodium hydroxide solution, saturated sodium chloride solution, and dried over anhydrous sodium sulphate. The solvent was removed by rotary evaporation to give a yellow oil which was purified by radial chromatography (gradient from hexane to 50% ethyl acetate/hexane). The solvent was removed by rotary evaporation to give 100 mg of the desired product as a yellow oil (14% yield). TLC (30% EtOAc/hexane) R$_f$ 0.25. $^1$H NMR (400 MHz, CDCl$_3$): 0.91 (t, J=7.4 Hz, 3H, CH$_2$CH$_3$), 1.51 (s, 6H, CCH$_3$), 1.4–1.6 (m, 2H, CH$_2$CH$_3$), 2.44 (t, J=7.4 Hz, 2H, SCH$_2$), 3.28 (m, 2H, NCH$_2$), 3.41 (m, 2H, NCH$_2$), 5.11 (brt, J=5.9 Hz, 1H, ArNH), 6.53 (m, 1H, ArH), 6.67 (d, J=8.3 Hz, 1H, ArH), 7.12 (dd, J=7.6, 1.6 Hz, 1H, ArH), 7.2–7.4 (m, 3H, ArH), ppm. $^{13}$C NMR (100 MHz, CDCl$_3$): 13.7, 22.8, 27.0, 32.1, 39.3, 43.3,49.7, 110.3, 116.7, 118.6, 132.1, 137.3, 149.1, 175.6 ppm. Mass spectrum m/z 312 (M$^+$), 117 (M$^+$-CONHCH$_2$CH$_2$NHC$_6$H$_5$SH).

EXAMPLE 18

2-N-[2-S-(butylthio)-2-methyl-1-oxopropyl] aminoacetic acid

The mercaptan prepared in Example 14 (1.6 g, 9.8 mmol) was reacted with 1.44 g sodium hydroxide (36.0 mmol) and 1.5 ml 1-bromobutane (14 mmol) by the method described in Example 15. This gave 1.1 g of the desired product as a yellow oil (48% yield). TLC (50% ethyl acetate/hexane) R$_f$ 0.38. $^1$H NMR (60 MHz, CDCl$_3$): 0.5–2.2 (m, 7H, CH$_2$CH$_2$CH$_3$), 1.47 (s, 6H, CCH$_3$), 2.50 (t, J=7 Hz, 2H, SCH$_2$), 4.00 (d, J=5 Hz, 2H, NCH$_2$), 7.73 (m, 1H, CONH), 10.10 (brs, 1H, COOH) ppm.

EXAMPLE 19

N[2-(((2-methyl-2-butylthio)propionyl)amino) acetyl]-2-(triphenylmethylthio)aniline The carboxylic acid prepared in Example 18 (0.49 g, 2.2 mmol) was reacted with 0.18 ml thionyl chloride (2.4 mmol) and 1.0 g of the aniline prepared in Example 6 (2.7 mmol) by the method described in Example 7. Triethylamine (1 ml, 10 mmol) was added after the addition of the aniline. The crude product was purified by column chromatography (gradient from hexane to 50% ethyl acetate/hexane) to give 0.62 g of the desired product as a red oil (48% yield). TLC (50% EtOAc/hexane) 0.79. $^1$H NMR (60 MHz, CDCl$_3$): 0.5–2.2 (m, 7H, CH$_2$CH$_2$CH$_3$), 2.53 (t, J=7 Hz, 2H, SCH$_2$), 3.67 (d, J=5 Hz, 2H, NCH$_2$), 6.0–8.8 (m, 21H, ArH) ppm.

EXAMPLE 20

N[2-(((2-methyl-2-butylthio)propionyl)amino) ethyl]-2-aminothiophenol

The diamide prepared in Example 19 (360 mg, 0.62 mmol) was reacted with 1.9 ml 1M borane-tetrahydrofuran complex (1.9 mmol) by the method described in Example 17. This gave 30 mg of the desired product as a yellow oil (18% yield). TLC (30% EtOAc/hexane) R$_f$ 0.32. $^1$H NMR (400 MHz, CDCl$_3$):0.85 (t, J=7.3 Hz, 3H, CH$_2$CH$_3$), 1.31 (m, 2H, CH$_2$CH$_3$), 1.48 (m, 2H, SCH$_2$CH$_2$), 1.50 (s, 6H, CCH$_3$), 2.46 (t, J=7.5 Hz, 2H, SCH$_2$), 3.28(m, 2H, NCH$_2$), 3.41 (m, 2H, NCH$_2$), 5.11 (brt, J=5.1 Hz, 1H, ArNH), 6.53 (t, J=7.5 Hz, 1H, ArH), 6.67 (d, J=8.2 Hz, 1H, ArH), 7.12 (dd, J=7.9, 1.5 Hz, 1H, ArH), 7.24 (m, 1H, ArH), 7.29 (m, 1H, CONH) ppm. $^{13}$C NMR (100 MHz, CDCl$_3$): 13.7, 22.2, 27.0, 29.7, 31.3, 39.2, 43.3, 49.7, 110.3, 116.7, 118.6, 132.1, 137.2, 149.0, 175.6 ppm. Mass spectrum m/z 326 (M$^+$).

EXAMPLE 21

2-N[2-Methyl-2-S(ethylthiol)-1-oxopropyl] aminoacetic acid

The mercaptan prepared in Example 14 (1.4 g, 7.9 mmol) was reacted with 1.2 g sodium hyroxide (30 mmol) and 1.9 g iodoethane (12 mmol) by the method described in Example 15. This gave 1.47 g of the desired product as a yellow oil (91% yield). TLC (50% ethyl acetate/hexane) R$_f$ 0.2. $^1$H NMR (60 MHz, CDCl$_3$): 1.23 (t, J=7 Hz, 3H, CH$_2$CH$_3$), 1.50 (s, 6H, CCH$_3$), 2.53 (q, J=7 Hz, 2H, SCH$_2$CH$_3$), 4.00 (d, J=5 Hz, 2H, NCH$_2$), 7.67 (m, 1H, CONH), 9.53 (brs, 1H, COOH) ppm.

EXAMPLE 22

N[2-(((2-methyl-2-ethylthio)propionyl)amino) acetyl]-2-triphenylmethylthio-aniline The carboxylic acid prepared in Example 21 (1.4 g, 6.8 mmol) was reacted with 1.04 g thionyl chloride (8.3 mmol) and 1.98 g of the aniline, prepared in Example 6, (5.4 mmol) by the method described in Example 7. The crude product was purified by column chromatography (gradient from hexane to 50% ethyl acetate/hexane) to give 1.37 g of the desired product as an orange solid (46% yield). TLC (50% EtOAc/hexane) R$_f$ 0.73. $^1$H NMR (400 MHz CDCl$_3$): 1.23 (t, J=7.4 Hz, 3H, CH$_2$CHH$_3$), 1.53 (s, 6H, CCH$_3$), 1.57 (q, J=7.5 Hz, 2H, CH$_2$CH$_3$), 3.63 (d, J=5.1 Hz, 2H, NCH$_2$), (td, J=7.6 Hz, 1H, ArH), 7.0–7.4 (m, 17H, ArH), 7.46 (m, 1H, CONH), 8.0(brs, 1H, ArCONH), 8.21 (d, J=8.5 Hz, 1H, ArH) ppm. $^{13}$C NMR (100 MHz, CDCl$_3$): 14.2, 24.0, 26.9, 43.7, 49.6, 71.7, 119.5, 120.2, 123.6, 127.1, 127.8, 129.6, 131.2, 137.6, 141.7, 143.5, 166.0, 175.2 ppm. Mass spectrum (FAB) m/z 555 (M$^+$+H), 553 (M$^+$–H).

EXAMPLE 23

N[2-(((2-methyl-2-ethylthio)propionyl) amino)ethyl]-2-aminothiophenol

The diamide prepared in Example 22 (1.25 g, 2.25 mmol) was reacted with 7.0 ml 1M borane-tetrahydrofuran complex (7.0mml) by the method described in Example 17. This gave 240 mg of the desired product as a yellow oil (36% yield). TLC (30% ethyl acetate/hexane) R$_f$ 0.23. $^1$H NMR (400MHz, CDCl$_3$): 1.16 (t, J=7.5 Hz, 3H, CH$_2$CH$_3$) 1.50 (s, 6HCHH$_3$), 2.50 (q, J=7.5 Hz, 2H), 3.28 (m, 2HNCH$_2$), 3.41 (m, 2HNCH$_2$), 5.10 (m, 1HArNH), 6.53 (m, 1HArNH), 6.67 (d, J=8.3 Hz, 1HArH), 7.12 (dd, J=7.7, 1.5 Hz, 1HArH), 7.24 (m, 1HArH), 7.28 (m, 1HCONH) ppm. $^{13}$C NMR (100 MHz, CDCl$_3$): 14.3, 24.1, 27.0, 39.3, 43.2, 49.8, 110.3, 116.7, 118.6, 132.1, 137.3, 149.0, 175.6 ppm.

EXAMPLE 24

2-(Propylthio)aniline

A solution of 3.2 g sodium hydroxide (80 mmol) in 13 ml water was added to a solution of 5.0 g 2-aminothiophenol(40 mmol) in 64 ml ethanol. The mixture was stirred at room temperature for 0.5 hour. Propyl iodide (7.37 g, 44 mol) was added and the mixture continued stirring for 16 hours. The mixture was treated with 0.5M sodium hydroxide, and extracted three times with ether. The organic layers were combined, washed with saturated sodium chloride solution, and dried over anhydrous sodium sulphate. The solvent was removed by rotary evaporation to give 5.7 g of a purple oil (85% yield). TLC (50% EtOAc/hexane) R$_f$ 0.82. $^1$H NMR (60 MHz, CDCl$_3$): 0.93 (t, J=6 Hz, 3H, CH$_2$CH$_3$), 1.50 (m, 2H, CH$_2$CH$_3$), 2.66 (t, J=6 Hz, 2H, SCH$_2$), 4.27 (brs, 2H, ArNH$_2$), 6.3–7.5 (m, 4H, ArH) ppm.

EXAMPLE 25

N[2-(((2-methyl-2-(4-methoxybenzylthio)) propionyl) amino)acetyl]-2-(propylthio)aniline The carboxylic acid prepared in Example 13 (3.25 g, 10.5 mmol) was reacted with 1.0 ml thioyl chloride (14 mmol) and 1.82 g of the aniline prepared in Example 24 (10.9 mmol) by the method described in Example 7. Triethylamine (1ml, 10 mmol) was added after the addition of the aniline. The crude product was purified by column chromatography (gradient from hexane to 40% ethyl acetate/hexane) to give 1.0 g of the desired product as an orange oil (21% yield). TLC (50% EtOAc/hexane) $R_f$ 0.60. $^1$H NMR (400 MHz, CDCl$_3$): 1.41 (t, J=7.4 Hz, 3H, CH$_2$CH$_3$), 1.55 (m, 2H, CH$_2$CH$_3$), 1.61 (s, 6H, CCH$_3$), 2.70 (t, J=7.4 Hz, 2H, SCH$_2$CH$_3$), 3.75 (s, 3H, OCH$_3$), 3.78 (s, 2H, SCH$_2$Ar), 3.98 (d, J=5.6Hz, 2H, NCH$_2$), 6.82 (d, J=8.7 Hz, 2H, ArH), 7.06 (t, J=7.5 Hz, 1H), 7.22 (d, J=8.7 Hz, 2H), 7.32 (m, 1H), 7.49 (m, 1H), 7.58 (m, 1H), 8.37 (d, J=8.1 Hz, 1H) 8.81 (brs, 1H, ArNHCO) ppm. $^{13}$C NMR (100 MHz, CDCl$_3$): 13.3, 22.7, 26.9, 34.1, 38.2, 44.5, 50.0, 55.2, 114.0, 120.2, 123.3, 124.3, 129.0, 129.4, 130.1, 135.0, 138.8, 158.7, 166.9, 175.4 ppm. Mass Spectrum (FAB) m/z 447 (M$^+$+H), 431 (447-CH$_4$), 294 (447-SCH$_2$C$_6$H$_4$OCH$_3$).

EXAMPLE 26

N[2-(((-methyl-2-(4-methoxybenzylthio))propionyl)amino)ethyl]-2-(propylthio)aniline The diamide prepared in Example 25 (1.43, 3.21 mmol) was reacted with 10.0 ml 1M borane-tetrahydrofuran complex (10.0 mmol) by the method described in Example 17. The crude product was purified by column chromatography (gradient from hexane to 15% ethyl acetate/hexane) to give 650 mg of the desired product as a clear oil (47% yield). TLC (30% EtOAc/hexane) $R_f$ 0.56. $^1$H NMR (60 MHz, CDCl$_3$): 0.93 (t, J=6 Hz, 3H, CH$_2$CH$_3$), 1.2–2.0 (m, 2H, CH$_2$CH$_3$), 1.53 (s, 6H, CCH$_3$), 2.63 (t, J=6 Hz, 2H, SCH$_2$CH$_2$), 3.1–3.6 (m, 4H, NCH$_2$CH$_2$), 3.66 (s, 2H, SCH$_2$Ar), 3.73 (s, 3H, OCH$_3$), 5.27 (brs, 1H, ArNH), 6.5–7.6 (m, 9H, ArH, CONH) ppm.

EXAMPLE 27

N[2-(((2-methyl-2-mercapto)propionyl) amino) ethyl]-2-(propylthio)aniline

The compound prepared in Example 26 (450 mg, 1.04 mmol) was reacted with 15 ml trifluoroacetic acid and 3 ml triethylsilane by the method described in Example 11. The mixture stirred at reflux, under nitrogen, for 55 minutes before adding the triethylsilane. The crude oil was purified by radial chromatography (gradient from hexane to 50% ethyl acetate/hexane) to give 292 mg of the desired product as a clear oil (90% yield). TLC (30% EtOAc/hexane) $R_f$ 0.56. $^1$H NMR (400 MHz CDCl$_3$): 0.97 (t, J=7.3 Hz, 3H, CH$_2$CH$_3$), 1.57 (m, 2H, CH$_2$CH$_3$), 1.59 (s, 6H, CCH$_3$), 2.14 (s, 1H, SH), 2.67 (t, J=7.3 Hz, 2H, SCHCH$_2$), 3.38 (m, 2H, NCH$_2$), 3.52 (m, 2H, NCH$_2$), 5.26 (brs, 1H, ArNH), 6.5–6.8 (m, 2H, ArH), 7.21 (m, 1H, CONH), 7.40 (dd, J=7.6, 1.6 Hz, 1H, ArH) ppm. $^{13}$C NMR (100 MHz, CDCl$_3$): 13.3, 23.0, 30.4, 37.0, 39.6, 43.1 47.8, 110.1, 117.1, 118.2, 129.9, 136.2, 148.8, 175.7, ppm. Mass Spectrum m/z 312 (M$^+$), 278 (M$^+$-H$_2$S), 180 (M$^+$-CH$_2$NHCOC(CH$_3$)$_2$SH).

EXAMPLE 28

2-(4-Methoxybenzylthio)aniline

2-Aminothiophenol (25 g, 0.2 mol) was reacted with 16 g sodium hydroxide (0.40 mol) and 34.8 g p-methoxybenzylchoride (0.22 mol) by the method described in Example 24. The mixture was stirred at room temperature for 16 hours. The precipitate was filtered from the reaction mixture, and recrystallised from ethyl acetate to give 23 g of the desired product as a light brown solid (47% yield). $^1$H NMR (60 MHz, CDCl$_3$): 3.66 (s, 3H), 3.73 (s, 2H), 4.13 (brs, 2H), 6.3–7.3(m, 8H) ppm. TLC (50% ethyl acetate/hexane) $R_f$ 0.80.

EXAMPLE 29

1-N-(tert-butoxycarbonyl)-2-N'-[2-S-(4-methoxybenzylthio)phenyl]2-oxodiaminoethane N-tert-Butoxycarbonylglycine-N-hydroxysuccinimide ester (17.7 g, 65 mmol) was suspended in 250 ml dichloromethane. The aniline prepared in Example 28 (20.7 g, 84.5 mmol) was added and the mixture was heated at reflux for 96 hours. The cooled mixture was washed with 0.5M hydrochloric acid, 0.5M sodium hydroxide solution, saturated sodium chloride solution, and dried over anhydrous sodium sulphate. The solvent was removed by rotary evaporation and the crude product was purified by column chromatography (gradient from hexane to 40% ethyl acetate/hexane) to give 22.6 g of the desired product as a clear oil (86% yield). $^1$HNMR (60 MHz, CDCl$_3$): 1.47 (s, 6H), 3.73 (s, 3H), 3.6–3.8 (m, 4H), 4.96 (brs, 1H), 6.3–7.5 (m, 7H), 8.33 (d, J=6 Hz, 1H) 8.80 (s, 1H) ppm. TLC (50% ethyl acetate/hexane) $R_f$ 0.59.

EXAMPLE 30

1-Amino-2-N-[2-S-(4-methoxybenzylthio) phenyl]-2-oxoaminoethane

The amide prepared in Example 29 (20.59 g, 0.051 mmol) was dissolved in 80 ml trifluoroacetic acid, and 80 ml water. The mixture was stirred under nitrogen for 2 hours, and the volatile material was removed by rotary evaporation. The residue was diluted with 100 ml 1M sodium hydroxide solution and then brought to pH 11.0 with 10M sodium hydroxide solution. The mixture was extracted with 3×100 ml dichloromethane. The organic layers were combined and washed with 100 ml 0.5M sodium hydroxide solution and 100 ml saturated sodium chloride solution. The organic layer was dried over anhydrous sodium sulphate, and the solvent was removed by rotary evaporation to give 14.96 g of a light purple solid (97% yield). $^1$H NMR (60 MHz, CDCl$_3$): 1.77 (s, 2H), 3.33 (s, 2H), 3.67 (s, 3H), 3.77 (s, 2H), 6.3–7.5 (m, 7H), 8.23 (d, J=7 Hz, 1H), 9.87 (brs, 1H) ppm. TLC (50% chloroform/ethyl acetate) $R_f$ 0.20.

EXAMPLE 31

1-Amino-2-N-[2-S-(4-methoxybenzylthio)phenyl] aminoethane

Lithium aluminium hydride (2.21 g, 58.3 mmol) was suspended in 75 ml tetrahydrofuran and cooled to 0° C. under nitrogen. The amide prepared in Example 30 (11.76 g, 38.9 mmol) in 125 ml tetrahydrofuran was added dropwise to the suspension and the mixture was stirred at room temperature for 64 hours. The mixture was cooled to 0° C. and 20 ml 50% ethyl acetate/tetrahydrofuran was added, followed by 20 ml 10% hydrochloric acid. The mixture was filtered through Celite and washed with 200 ml ethyl acetate, 50 ml 1M sodium hydroxide solution, and then another 200 ml ethyl acetate. The solvent was removed from the filtrate by rotary evaporation, and the residue was treated with 200 ml ethylacetate and 50 ml 0.5M sodium hydroxide solution. The aqueous layer was separated and washed with 50 ml 0.5M sodium hydroxide solution, 50 ml saturated sodium chloride solution, and dried over anhydrous sodium sulphate. Removal of the solvent by rotary evaporation gave 11.17 g of a thick yellow oil (99% yield). $^1$H NMR (60 MHz, CDCl$_3$): 1.13 (s, 2H), 2.5–3.5 (m, 4H), 3.67 (s, 3H), 3.80 (s, 2H), 5.20 (m, 1H), 6.3–7.5 (m, 8H) ppm. TLC (86% ethylacetate/10% methanol/3% water/1%25M ammonium hydroxide) $R_f$ 0.46.

EXAMPLE 32

2-Methyl-2-(2-propenylthio)propionic acid

The carboxylic acid prepared in Example 1 (5.68 g, 23.7 mmol) was reacted with 44 ml trifluoroacetic acid and 4 ml triethylsilane by the method described in Example 11. After the volatile material was removed by rotary evaporation the residue was treated with hexane and the mixture was filtered through a Buchner funnel. The solvent was removed from the filtrate by rotary evaporation to yield 3.10 g of the crude mercaptan as a white oil.

The crude mercaptan (3.10 g) was dissolved in 125 ml ethanol. To this solution was added 3.33 g sodium hydroxide (83.2 mmol) in 22 ml water and the mixture was stirred at room temperature for 30 minutes. Allyl bromide (3.33 ml, 38.5 mmol) was added and the mixture was stirred under nitrogen for 1 hour. The volatile mateiral was removed by rotary evaporation and the residue was dissolved in ether and water. The mixture was extracted three times with 2M sodium hydroxide solution. The aqueous layers were combined and brought to pH 2.0 with 1M hydrochloric acid. The mixture was extracted three times with ethyl acetate. The organic layers were combined, dried over sodium sulphate, and the solvent was removed by rotary evaporation to give 1.75 g of the desired product as a yellow oil. $^1$H NMR (60 MHz, CDCl$_3$): 1.50 (s, 6H), 3.30 (d, J=6 Hz, 2H), 4.7–6.3 (m, 3H), 12.03 (s, 1H) ppm. TLC (50% ethyl acetate/hexane) R$_f$ 0.67.

EXAMPLE 33

N[2-(((2-methyl-2-allythio)propionyl)amino)ethyl]2-(4-methoxybenzylthio) aniline The carboxylic acid prepared in Example 32 (705 mg, 4.41 mmol) was reacted with 0.38 ml thionyl chloride (5.21 mmol) and 1.60 g of the amine prepared in Example 31 (5.56 mmol) by the method described in Example 7. The crude product was purified by column chromatography (gradient from hexane to 20% ethyl acetate/hexane) to give 890 mg of the desired product a clear oil (47% yield). Anal. calcd. for C$_{23}$H$_{30}$N$_2$O$_2$S$_2$: C, 64.15; H, 7.02; N, 6.50; S, 14.89. Found: C.64.09, H, 7.07; N, 6.43; S, 14.63. $^1$H NMR (400 MHz, CDCl$_3$): 1.52 (s, 6H), 3.16 (d, J=7.0 Hz, 2H), 3.23 (m, 2H), 3.42 (m, 2H), 3.77 (s, 3H), 3.81 (s, 2H), 5.02 (m, 1H), 5.11 (m, 1H), 5.13 (m, 1H), 5.75 (m, 1H), 6.59 (m, 1H), 6.62 (m, 1H), 6.77 )d, J=8.7 Hz 2H), 7.04 (d, J=8.7 Hz, 2H), 7.20 (m, 1H), 7.21 (m, 1H), 7.25 (m, 1H) ppm. $^{13}$C NMR (100 MHz, CDCl$_3$): 27.0, 33.4, 39.4, 39.4, 43.3, 50.1, 55.3, 110.0, 113.8, 117.1, 117.6, 117.8, 130.0, 130.4, 133.6, 136.8, 149.2, 158.7, 175.2 ppm. Mass Spectrum m/z 430 (M$^+$). TLC (30% ethylacetate/hexane) R$_f$ 0.36.

EXAMPLE 34

N[2-(((2-methyl-2-alkylthio)propionyl)amino)ethyl ]-2-aminothiophenol

The compound prepared in Example 33 (340 mg, 0.79 mmol) was reacted with 1.6 ml trifluoroacetic acid and 0.14 ml triethylsilane (0.88 mmol) by the method described in Example 11. The mixture stirred at reflux, under nitrogen, for 1.5 hours before adding the triethylsilane. The crude oil was purified by radial chromatography (gradient from hexane to 50% ethyl acetate/hexane) to give 30 mg of the desired product as a yellow oil (12% yield). $^1$H NMR (400 MHz, CDCl$_3$): 1.52 (s, 6H), 3.16 (d, J=6.90 Hz, 2H), 3.28 (m, 2H), 3.41 (m, 2H), 5.03 (d, J=9.9 Hz, 1H), 5.11 (m, 1H), 5.13 (m, 1H), 5.76 (m, 1H), 6.53 (t, J=7.5 Hz, 1H), 6.68 (d, J=8.1 Hz, 1H), 7.12 (dd, J=7.7, 1.3 Hz), 7.22 (m, 1H), 7.24 (m, 1H) ppm. $^{13}$C NMR (100MHz, CDCl$_3$): 27.0, 33.4, 39.3, 43.2, 50.1,110.3, 116.7, 117.8, 132.1, 133.6, 137.3, 149.0, 175.4 ppm. TLC (40% ethyl acetate/hexane) R$_f$ 0.39.

EXAMPLE 35

2-Methyl-2-(2-propynylthio)propionic acid

The carboxylic acid prepared in Example 1 (5.03 g, 21.0 mmol) was reacted with 40 ml trifluoroacetic acid and 5 ml triethylsilane by the method described in Example 11. After the volatile material was removed by rotary evaporation, the residue was treated with hexane and the mixture was filtered through a Buchner funnel. The solvent was removed from the filtrate by rotary evaporation to yield 2.95 g of the crude mercaptan as a white oil.

The crude mercaptan (2.95 g, 24.6 mmol) was suspended in 100 ml tetrahydrofuran. Sodium hydroxide (1.18 g, 29.5 mmol) in 3 ml water was added and the mixture stirred at room temperature for 0.5 hours. Propargyl chloride (2.0 g, 27.04 mmol) was added and the mixture stirred at room temperature, under nitrogen, for an additional 18 hours. 0.5M sodium hydroxide solution was added and the mixture was washed 2 times with ether. The aqueous layer was acidified with 1M hydrochloric acid and extracted 3 times with ether. The organic layers were combined, dried over anhydrous sodium sulphate, and the solvent was then removed by rotary evaporation to give 2.04 g of the desired product as a yellow oil (52% yield). $^1$H NMR (60 MHz, CDCl$_3$): 1.57 (s, 6H), 2.23 (m, 1H), 3.40 (d, J=3 Hz, 2H), 12.17 (s, 1H) ppm. TLC (50% ethyl acetate/hexane) R$_f$ 0.67.

EXAMPLE 36

N[2-(((2-methyl-2-(2-propynylthio))propionyl) amino) ethyl]-2-(4-methoxy-benzylthio)aniline The carboxylic acid prepared in Example 35 (0.64 g, 4.0 mmol) was reacted with 0.34 ml thionyl chloride (4.7 mmol) and 1.5 g of the amine, prepared in 10 Example 31 (5.2 mmol), by the method described in Example 7. This gave 0.72 g of the desired product as a brown oil (43% yield). Anal. Calcd. for C$_{23}$H$_{28}$N$_2$S$_2$O$_2$: C, 64.45; H, 6.58; N, 6.54; S, 14.96. Found: C, 64.62, H, 6.43; N, 6.48; S, 15.01. $^1$H NMR(400 MHz, CDCl$_3$): 1.55 (S, 6H), 2.17 (t, J=2.7 Hz, 1H), 3.25 (m, 1H), 3.25 (d, J=2.7 Hz, 2H), 3.43 (m, 2H), 3.77 (s, 3H), 3.82 (s, 2H), 5.18 (brs, 1H), 6.58 (td, J=7.5, 1.2 Hz, 1H), 6.62 (d, J=8.1 Hz, 1H), 6.76 (d, J=8.7 Hz, 2H), 7.05 (d, J=8.7 Hz, 2H), 7.19 (m, 2H), 7.26 (dd, J=77, 1.7 Hz, 1H)ppm. $^{13}$C NMR (100 MHz, CDCl$_3$): 18.0, 26.6, 39.4, 43.2, 50.4, 55.2, 71.8, 79.5, 109.9, 113.7, 117.1, 117.5, 130.0, 130.4, 136.9, 149.1, 158.6, 174.6 ppm. Mass Spectrum m/z 428 (M$^+$) 307 (M$^+$-CH$_2$C$_6$H$_4$OCH$_1$). TLC (50% ethyl acetate/hexane) R$_f$ 0.60.

EXAMPLE 37

N[2-(((2-methyl-2-(4-methoxybenzylthio)) propionyl) amino)ethyl]-2-(4-methoxy-benzylthio) aniline The amine prepared in Example 31 (750 mg, 2.60 mmol) was reacted with the carboxylic acid prepared in Example 1 (496 mg, 2.07 mmol) and 0.18 ml thionyl chloride (2.47 mmol) by the method described in Example 7. The crude product was purified by column chromatography (gradient from hexane to 20% ethyl acetate/hexane) to give 800 mg, of the desired product as a yellow oil (76% yield). $^1$H NMR (400 MHz, CDCl$_2$): 1.54 (s, 6H), 3.18 (m, 2H), 3.37 (q, J=5.9 Hz, 2H), 3.66 (s, 2H), 3.74 (s, 3H), 3.76 (s, 3H), 3.79, (s, 2H), 5.13 (m, 1H), 6.5–6.7 (m, 2H), 6.7–6.8 (m, 4H), 7.02 (d, J=8.7 Hz, 2H), 7.09 (d, J=8.7 Hz, 2H), 7.20(m, 1H), 7.2–7.3 (m, 2H) ppm. $^{13}$C NMR (100 MHz, CDCl$_3$): 26.9, 34.2, 39.3, 39.4, 43.4, 50.4, 55.2, 110.0, 113.7, 114.0, 117.1, 117.6, 129.0, 129.9, 130.0, 130.4, 136.8, 149.2, 158.6, 158.7, 175.0 ppm. Mass spectrum m/z 510 (M$^+$). TLC (30% ethyl acetate/hexane) R$_f$ 0.27.

EXAMPLE 38

N[2-(((2-methyl-2-mercapto)propionyl) amino) ethyl-2-(4-methoxybenzylthio)-aniline A The compound prepared in Example 37 (0.68 g, 1.3 mmol) was reacted with 3 ml trifluoroacetic acid and 0.27 ml triethylsilane by the method described in Example 11 to give 0.23 g of a yellow oil (44% yield).

B Alternatively, Example 38 was prepared as follows:

The mercaptan prepared in Example 2 (1.20 g, 10.0 mmol), 2.55 g dicyclohexylcarbodiimide (12.4 mmol), 1.2 g, N-hydroxysuccinimide (10.7 mmol), and 3.06 g of the amine prepared in Example 31 (10.6 mmole) were dissolved in 100 ml tetrahydrofuran, and stirred at room temperature, under argon for 17 hours. The mixture was treated with 30 ml 0.5M sodium hydroxide solution, and extracted with 3×50 ml ethyl acetate. The organic layers were combined and washed with 30 ml 0.5M sodium hydroxide solution, and extracted with 3×50 ml ethyl acetate. 2×75 ml 0.5M hydrochloric acid and 2×75 ml saturated sodium chloride solution. The organic layer was dried over anhydrous sodium sulphate, and the solvent was removed by rotary evaporation to give the crude product. This was purified by column chromatography (gradient from chloroform to 50% ethyl acetate/chloroform) to give 1.48 g of the desired product as a yellow oil (38% yield). $^1$H NMR(400 MHz, CDCl$_3$): 1.58 (s, 6H), 2.13 (s, 1H), 3.26 (m, 2H), 3.43 (m, 2H), 3.77 (s, 3H), 3.82 (s, 2H), 5.17 (brs, 1H), 6.5–6.7 (m, 2H), 6.77 (d, J=8.7 Hz, 2H) 7.04 (d, J=8.7 Hz, 2H), 7.1–7.3 (m, 3H) ppm. $^{13}$C NMR (100 MHz, CDCl$_3$): 30.4, 39.4, 39.7, 43.1, 47.7, 55.3, 110.1, 113.8, 117.2, 117.6, 130.0, 130.4, 136.7, 149.1, 158.7, 175.6. Mass Spectrum m/z 390 (M$^+$), 358 (M$^+$-CH$_{3O}$H), 356 (M$^+$-H$_2$S). TLC (40% ethyl acetate/hexane) R$_f$ 0.46.

EXAMPLE 39

N[2-(((2-methyl-2-(2-hydroxyethylthio))propionyl) amino) ethyl]-2-(4-methoxybenzylthio)aniline The mercaptan prepared in Example 38A (180 mg, 0.46 mmol) was dissolved in 30 ml freshly distilled tetrahydrofuran. Sodium hydride (30 mg in 50% mineral 20 oil, 0.63 mmol) was washed with 3×5 ml hexane and added to the reaction mixture. The solution was stirred under nitrogen for 5 minutes. 1-Bromoethanol (0.035 ml, 0.5 mmol) was added and the mixture continued stirring at room temperature for 3 hours. Methanol (5 ml) was added and the mixture was diluted with 200 ml ethyl acetate. The mixture was washed with 50ml water and 50 ml saturated sodium chloride solution, and dried over anhydrous magnesium sulphate. The solvent was removed by rotary evaporation to give a crude oil. This was purified by radial chromatography (gradient from petroleum ether to 60% ethyl acetate/ petroleum ether) to give 100 mg clear oil (50% yield). IR neat: 3600–3200 cm$^{-1}$, 2980 2940, 1650 1600 cm$^{-1}$. $^1$H IVMR (400 MHz, CDCl$_3$): 1.52 (s, 6H), 2.05 (brs, 1H), 2.69 (t, J=6.08 1H), 3.21 (m, 2H), 3.41 (m, 2H), 3.65 (t, J=6.0 Hz, 2H), 3.78 (s, 3H), 3.82 (s, 2H), 5.09 (brs, 1H), 6.5–6.7 (m, 2H), 6.78 (d, J=8.5 Hz, 2H), 7.04 (d, J=8.7 Hz, 2H), 7.20 (td, J=7.8, 1.6 Hz, 1H), 7.25–7.30 (m, H) ppm. $^{13}$C NMR (100 MHz, CDCl$_3$). 27.1, 33.2, 39.5, 39.6, 43.3, 49.8, 55.3, 60.9, 110.2, 113.8, 117.3, 17.6, 130.0, 130.4, 136.7, 149.1, 158.7, 175.2. Mass spectrum m/z 434 (m+), 416 (m+-H$_{2O}$), 401 (416-CH$_2$), 358 (M+-C$_2$H$_4$SO). TLC (50% ethyl acetate/ hexane) R$_f$ 0.22.

EXAMPLE 40

N[2-(((-methyl-2-(methoxycarbonylmethylenethio)) propionyl)amino)ethyl]-2-(4-methoxybenzylthio) aniline The mercaptan prepared in Example 38A (290 mg, 0.74 mmol) was reacted with 24 mg sodium hydride (1.0 mmol) and 125 mg methyl bromoacetate (0.82 mmol) by the method described in Example 39. The crude product was purified by radial chromatography (gradient from hexane to 30% ethyl acetate/hexane) to give 0.19 g of the desired product as a colourless oil (56% yield). Anal.Calcd. for C$_{23}$H$_{30}$N$_2$S$_2$O$_4$: C, 59.71; H, 6.54; N, 6.06; S, 13.86. Found: C, 59.83; H, 6.55; N, 5.94; S, 13.96. $^1$H NMR(400 MHz, CDCl$_3$): 1.53 (s, 6H), 3.24 (m, 2H), 3.31 (s, 2H), 3.44 (m, 2H), 3.64 (s, 3H), 3.77 (s, 3H), 3.81 (s, 2H), 5.18 (m, 1H), 6.5–6.7 (m, 2H), 6.77 (d, J=8.7 Hz, 2H) 7.05 (d, J=8.7 Hz, 2H), 7.1–7.4 25 (m, 3H) ppm. $^{13}$C NMR (100 MHz, CDCl$_3$): 26.7, 32.4, 39.4, 43.2, 50.4, 52.6, 55.3, 110.0, 113.7, 117.0, 117.6, 130.0, 130.1, 130.4, 136.8, 149.1, 158.7, 170.5, 174.4 ppm. Mass spectrum m/z 462 (M$^+$), 431 (M$^-$-COOCH$_3$). TLC (40% ethyl acetate/hexane) R$_f$ 0.31.

EXAMPLE 41

N[2-(((2-methyl-2-(3-aminopropylthio))propionyl) amino) ethyl]-2-(4-methoxybenzylthio)aniline The mercaptan prepared in Example 38B (250 mg, 0.64 mmol) was reacted with 33 mg sodium hydrid (1.4 mmol) and 154 mg 3-bromopropylamino hydrobromide (0.7 mmol) by the method described in Example 39. The reaction mixture was stirred for 19 hours. The crude oil was purified by radial chromatography (86% ethyl acetate/10% methanol/3% water/1% 15M ammonium hydroxide) to give 180 mg yellow oil (63% yield). IR (neat): 3400–3200, 1650 cm$^{-1}$. $^1$H NMR(400 MHz, CDCl$_3$): 1.50 (s, 6H), 1.61 (m, 2H), 1.71 (brs, 2H), 2.51 (t, J=7.35, Hz, 2H), 2.66 (t, J=6.8 Hz, 2H), 3.22 (m, 2H), 3.44 (m, 2H), 3.77 (s, 3H), 3.81 (s, 2H), 5.14 (brs, 1H), 6.58 (m, 1H), 6.61 (m, 1H), 6.77 (d, J=8.6 Hz, 2H), 7.05 (d, J=8.6 Hz, 2H), 7.19 (m, 1H), 7.25 (dd, J=1.6, 7.5 Hz, 1H), 7.37 (brt, J=5.5 Hz, 1H)ppm. $^{13}$C NMR (100 MHz, CDCl$_3$): 27.0, 27.3, 32.4, 39.3, 39.4, 41.0, 43.4, 49.8, 55.2, 109.9, 113.7, 117.1, 117.5, 130.0, 130.3, 130.4, 136.7, 149.1, 158.6, 175.4 ppm. Mass spectrum m/z 447 (M$^+$), 414 (M$^+$-SH), 326 (M$^+$-CH$_2$C$_6$H$_4$OCH$_3$). TLC (86% ethyl acetate/10% methanol/3% water/1% 15M ammonium hydroxide) R$_f$ 0.30.

EXAMPLE 42

2-S-(4-Methoxybenzylthio-2-methylpropionamide

The carboxylic acid prepared in Example 1 (4.02 g, 16.7 mmol) was dissolved in 50 ml dichloromethane and treated with 1.77 ml thionyl chloride (24.3 mmol). The mixture was stirred at reflux for 2 hours under nitrogen. The volatile material was removed by rotary evaporation and 10 ml ammonium hydroxide was added to the residue at 0° C. The mixture was stirred for 30 minutes, and the volatile material was removed by rotary evaporation. The residue was treated with 50 ml ethyl acetate and 50 ml water. The aqueous layer was separated and washed with 2×50 ml ethyl acetate. The organic layers were combined and washed with 2×50 ml 2M sodium hydroxide solution, 2×50 ml 1M hydrochloric acid, and saturated sodium chloride solution. The organic layer was dried over anhydrous sodium sulphate, and the solvent was removed by rotary evaporation to give 2.33 g of the desired product as a yellow solid (58% yield). $^1$H NMR (400 MHz, CDCl$_3$): 1.56 (s, 6H), 3.75 (s, 2H), 3.79 (s, 3H), 5.70 (brs, 1H), 6.74 (brs, 1H), 6.83 (d, J=8.7 Hz, 2H), 7.20 (d, J=8.7 Hz, 2H) ppm. $^{13}$C NMR (100 MHz, CDCl$_3$): 26.8, 34.3, 49.9, 55.3, 114.1, 129.0, 130.1, 158.8, 177.3 ppm. Mass spectrum m/z 239 (M$^+$). TLC (50% ethyl acetate/hexane) R$_f$ 0.21.

EXAMPLE 43

1-Amino-2-S-(4-methoxybenzylthio)-2-methylpropane

The amide prepared in Example 42 (2.33 g, 9.75 mmol) was reacted with lithium aluminium hydride (890 mg, 23.4 mmol) by the method described in Example 31. The crude product was purified by radial chromatography (86% ethyl acetate/10% metanol/3% water/1% 15M ammonium hydroxide) to give 878 mg of the desired product as a yellow oil (40% yield). NMR (60 MHz, CDCl$_3$): 1.53 (s, 6H), 3.77 (s, 5H), 6.0 (brs, 2H), 6.5–7.8 (m, 4H) ppm.

EXAMPLE 44

N-[2-S-4-methoxybenzylthio)-2-methylpropyl] bromoacetamide

The amine prepared in Example 43 (180 mg, 0.80 mmol) was dissolved in 3 ml dichloromethane. Bromoacetylchloride (110 mg, 0.70 mmol) in 0.5 ml dichloromethane was added dropwise and the mixture was stirred at room temperature under nitrogen for 2.5 hours. The volatile material was removed by rotary evaporation and the residue was treated with 5 ml ether and 5 ml 1M hydrochloric acid. The organic layer was separated and washed with 2×5 ml 1M hydrochloric acid, 2×5 ml 0.5M sodium hydroxide solution and 5 ml saturated sodium chloride solution. The organic layer was dried over sodium sulphate and the solvent was removed by rotary evaporation to give 130 mg of the desired product as a yellow oil (54% yield). $^1$H NMR (60M Hz, CDCl$_3$): 1.30 (s, 6H), 3.20 (d, J=6 Hz, 2H), 3.5–4.0 (3×5, 7H), 6.5–7.5 (m, 5H) ppm.

EXAMPLE 45

N[2-oxo-2(N$^1$(2-methyl-2-(4-methoxybenzylthio)) propyl) amino)ethyl]-2-(methylthio)aniline The bromide prepared in Example 44 (130 mg, 0.38 mmol) was dissolved in 1 ml ethanol. To this solution was added 2.0 ml 2-(methylmercapto)aniline (16 mmol) and the mixture was stirred at room temperature under nitrogen for 14 hours. The mixture was warmed to 60° C. and stirred an additional 50 minutes. The mixture was then treated with 5×10 ml 1M hydrochloric acid, 10 ml 0.5M sodium hydroxide solution, and saturated sodium chloride solution. The organic layer was dried over anhydrous sodium sulphate, and the solvent was removed by rotary evaporation to give a crude brown oil. This was purified by radial chromatography (gradient from hexane to 80% ethyl acetate/hexane) to give 40 mg of the desired product as a colourless oil (26% yield). $^1$H NMR (400 MHz, CDCl$_3$): 1.22 (s, 6H), 2.32 (s, 3H), 3.24 (d, J=5.9 Hz, 2H), 3.52 (s, 2H), 3.76 (s, 3H), 3.87 (d, J=5.1 Hz, 2H), 5.56 (brt 1H), 6.54 (d, J=8.0 Hz, 1H), 6.72 (d, J=8.5 Hz, 2H), 6.79 (t, J=7.5 Hz, 1H), 7.01 (d, J=8.5 Hz, 2H), 7.11 (brt, 1H), 7.20 (m, 1H), 7.47 (m, 1H) ppm. $^{13}$C NMR (100 MHz, CDCl$_3$): 18.6, 6.7, 32.2, 46.5, 47.1, 48.7, 48.7, 55.4, 110.8, 114.0, 119.1, 121.0, 129.8, 129.9, 131.2, 134.3, 147.3, 158.7, 170.4 ppm. Mass spectrum m/z 404 (M$^+$). TLC (50% ethyl acetate/hexane) R$_f$ 0.39.

EXAMPLE 46

N[2-oxo-2-(N-((2-methyl-2-thio)propyl)amino) ethyl]2-(methylthio)aniline

The compound prepared in Example 45 (10.7 mg, 0.27 mmol) was reacted with 2.5 ml trifluoroacetic acid and 1 ml triethylsilane by the method described in Example 11 to give 40 mg of the desired product as a 15 clear yellow oil (52% yield). IR (neat): 3300–3400, 2980, 2940, 2585, 1700–1650 cm–1. $^1$H NMR(400 MHZ, CDCl$_3$):1.28 (s, 6H), 1.44 (s, 1H), 2.38 (s, 3H), 3.34 (d, J=6.4 Hz, 2H) 3.92 (s, 2H), 5.54 (brs, 1H), 6.56 (d, J=8.1 Hz, 1H), 6.79 (tJ=8.0 Hz, 1H), 7.11 (brs, 1H), 7.21 (m, 1H), 7.44 (m, 1H) ppm. $^{13}$C NMR (100 MHz, CDCl$_3$): 18.5, 29.9, 45.3, 48.6, 51.8, 110.8, 119.2, 121.2, 129.5, 133.9, 147.0, 170.3 ppm. Mass spectrum m/z 284 (M), 266 (M$^+$-H$_2$O), 250 (M$^+$-H$_2$S). TLC (50% EtOAc/hexane) R$_f$ 0.30.

EXAMPLE 47

N[2-(((2-methyl-2-chloroethylthio))propionyl) amino) ethyl]-2-(4-methoxybenzYlthio)aniline The mercaptan prepared in Example 388 (0.44 g, 1.1 mmol) was reacted with 65 mg sodium hydride (1.4 mmol) and 0.15 ml 1-bromo-2-chlorethane (1.5 mmol) by the method described in Example 39. The crude product was purified by radial chromatograPhY (gradient from hexane to 25% ethyl acetate/hexane) to give 0.33 g of the desired product as a yellow oil (65% yield). Anal. Calcd. for C$_{22}$N$_2$O$_2$S$_2$Cl:58.32; H, 6.45; N, 6.18; Cl, 7.06; S,14.15. Found: C, 58.91; H, 6.36; N, 6.26; Cl, 7.09; S, 13.89. IR (neat): 3360, 3000, 2960, 2920, 2830, 1650 cm$^{-1}$. $^1$H NMR (400 MHz, CDCl$_3$): 1.5, (s, 6H), 2.86 (t, J=7.3 Hz, 2H), 3.22, (m, 2H), 3.43 (m, H), 3.55 (t, J=7.2 Hz, 2H), 3.77 (s, 3H), 3.81 (s, H), 5.11 (brs, 1H), 6.5–6.7 (m, 2H), 6.78 (d, 2H), 7.04 (d, 2H), 7.11 (m, 1H), 7.20 (m, 1H), 7.26 (m, 1H) ppm. $^{13}$C NMR (100 MHz, CDCl$_3$): 26.9, 32.6, 39.4, 42.9, 43.2, 49.9, 55.3, 110.0, 113.7, 117.2, 117.6, 130.0, 130.4, 136.8, 149.1, 158.7, 174.9 ppm. Mass spectrum m/z 452. TLC (50% ethyl acetate/hexane) R$_f$ 0.62.

EXAMPLE 48

N[2-(((2-methyl-2-(2-cyanoethylthio))propionyl) amino) ethyl]-2-(4-methoxybenzylthio)aniline The mercaptan prepared in Example 38B (0.40 g, 1.0 mmol) was reacted with 55 mg sodium hydride (1.2 mmol) and 3-bromo-propionitrile (0.10 ml, 1.2 mmol) by the method described in Example 39. The crude product was purified by radial chromatography (gradient from hexane to 75% chloroform/hexane) to give 0.24 g of the desired product as a yellow oil (50% yield). Anal.Calcd. for C$_{23}$H$_{29}$N$_3$O$_2$S$_2$: C, 62.27; H, 6.59; N, 9.47, s, 14.45. Found: C, 62.44; H, 6.61; N, 9.39; S, 14.05. IR (neat): 3380, 3010, 2930, 2250, 1660. $^1$H NMR(400 MHz, CDCl$_3$): 1.52 (s, 6H), 2.50 (t, J=6.9 Hz, 2H), 2.73 (t, J=6.9 Hz, 2H), 3.25 (m, 2H), 3.46 (m, 2H), 3.77 (s, 3H), 3.82 (s, 2H), 5.12 (brs, 1H), 6.59 (m, 1H), 6.78 (d, J=8.5 Hz, 2H), 7.05 (d, J=8.5 Hz, 2H), 7.1–7.3 (m, 2H) ppm. $^{13}$C NMR (100 MHz, CDCl$_3$): 18.2, 25.6, 26.7, 39.4, 43.2, 49.9, 55.3, 110.0, 113.7, 117.2, 117.5, 118.1, 130.0, 130.2, 130.4, 136.7, 149.1, 158.6, 174.6 ppm. Mass spectrum m/z 443 (M$^+$), 410 (M$^+$-SH). TLC (90% chloroform/ethyl acetate) R$_f$ 0.38.

EXAMPLE 49

$^{99m}$Tc complex of N[2-(((-methyl-2-methylthio)) propionyl)amino)ethyl]-2-aminothiophenol N[2-(((2-ethyl-2-methylthio))propionyl)amino) ethyl]-2-aminothiophenol, Example 8, (1 mg, 3.5×10$^{-3}$ mmol) was dissolved in 1 ml nitrogen purged ethanol. Generator eluted Na$^{99m}$TcO$_4$ (0.2 ml, 4–40 mCi) was added to the solution, followed by 0.1 ml stannous chloride solution (1mM SnCl$_2$ in 0.1M hydrochloric acid). The mixture was incubated for 15 minutes, and filtered through an FG filter to yield the crude product. TLC (50% ethyl acetate/hexane on silica gel) R$_f$ 0.37, 56% radiochemical purity.

Normal saline (2 ml) was added to the mixture, and the complex was purified by elution through a 20 Waters C-18 Sep-pak (30% ethyl acetate/hexane wash, then product elution with 50% ethyl acetate/hexane). The purity of the complex was measured by TLC and HPLC. TLC (50% ethyl acetate/hexane on silica) R$_f$ 0.37, radiochemical purity 96%. HPLC(Waters Radial-Pak C-18, 70% acetonitrile/water, 2.0 ml/min. R$_t$ 4.23 min, radiochemical purity >99%. electrophoresis (0.1M NaH$_2$PO$_4$, pH 6.8, 250 volts, 25 min) neutral.

EXAPMLE 50

$^{99m}$Tc complex of N[2-(((methyl-2-mercapto) propionyl)amino)ethyl]-2-methylthio aniline N[2-(((methyl-2-mercapto)propionyl)amino) ethyl]-2-methylthioaniline, Example 11, (1 mg) was dissolved in 1 ml nitrogen purged ethanol. 0.1M Hydrochloric acid (0.1 ml) and 0.005 ml 1 mM stannous chloride were added to the mixture, followed by 1 ml generator eluate $^{99m}$Tc sodium pertechnetate (5–80mCi). The mixture was heated at 90° C. for 20 minutes. TLC (50% ethyl acetate/hexane) R$_f$ 0.60, radiochemical purity 96%. HPLC (Novo Pak C18, 70% acetonitrile/water, 2.0 ml/min) R$_t$ 33.6 min, radiochemical purity 97%. Electrophoresis (0.05M NaH2PO4, pH 4.5, 3000 volts, 30 min) neutral.

EXAMPLE 51

$^{99m}$Tc complex of N[2-(((2-methyl-2-propylthio) propionyl)amino)ethyl]-2-amino-thiophenol N[2-2(((2-methyl-2-propylthio)propionyl) amino)ethyl]-2-aminothiophenol, Example 17, was reacted with $^{99m}$Tc sodium pertechnetate by the method described in Example 49. TLC (50% ethyl acetate/hexane) R$_f$ 0.50, radiochemical purity 91%. HPLC (Radial-Pak C18, 70% acetonitrile/water, 2.0 ml/min R$_t$ 5.3 min, radiochemicalpurity 99.9%. electrophoresis (0.1M NaH$_2$PO$_4$, pH 6.8, 250 volts, 25 min) neutral.

EXAMPLE 52

$^{99m}$Tc complex of N[2-(((2-methyl-2-butylthio) propionyl)amino)ethyl]-2-amino-thiophenol N[2-(((2-methyl-2-butylthiopropionyl)amino) ethyl]-2-aminothiophenol, Example 20, was reacted with $^{99m}$Tc sodium pertechnetate by the method described in Example 49. TLC (50% ethyl acetate/hexane) R$_f$ 0.63, radiochemical purity 85%. HPLC (Radial-Pak C$_{18, 70}$% acetonitrile/water, 2.0 ml/min) R$_t$ 4.8 min, radiochemical purity 92%.

EXAMPLE 53

$^{99m}$Tc complex of N[2-(((2-methyl-2-ethylthio) propionyl)amino)ethyl]-2-amino-thioplhenol N[2-(((2-methyl-2-ethylthio)propionyl)amino) ethyl]-2-aminothiophenol, Example 23, was reacted with $^{99m}$Tc sodium pertechnetate by the method described in Example 49. TLC (50% ethyl acetate/hexane) R$_f$ 0.35, radiochemical purity 91%. HPLC (Radial-Pak C18, 70% acetonitrile/water, 2.0 ml/min) R$_t$ 5.23 min, radiochemical purity 95%.

EXAMPLE 54

$^{99m}$Tc N[2-(((2-methyl-2-mercapto)propionyl) amino) ethyl]-2-propylthioaniline N[2-(((2-methyl-2-mercapto) propionyl)amino) ethyl]-2-propylthioaniline, Example 27, was reacted with $^{99m}$Tc sodium pertechnetate by the method described in Example 49. TLC (50% ethyl acetate/hexane) R$_f$ 0.60, radiochemical purity 88%. HPLC (Radial-Pak C18, 70% acetonitrile/water, 2.0 ml/min) R$_t$ 6.1 min, radiochemical purity 95%. Electrophoresis (0.1M NaH$_2$PO$_4$, pH 6.8, 200 volts, 30 min) neutral.

EXAMPLE 55

$^{99m}$Tc complex of N[2-(((2-methyl-2-allylthio) propionyl) amino)ethyl]-2-(4-methoxybenzylthio) aniline N[2-(((2-methyl-2-allylthio)propionyl)amino) ethyl]-2-(4-methoxybenzylthio)aniline, Example 33, was reacted with $^{99m}$Tc sodium pertechnetate by the method described in Example 49. TLC (50% ethyl acetate/hexane) R$_f$ 0.64, radiochemical purity 91%. HPLC (Radial-Pak C$_{18}$, 70% acetonitrile/water, 2.0 ml/min) R$_t$ 4.8 min, radiochemical puity 93%. Electrophoresis (0.1M NaH$_2$PO$_4$, pH 6.8, 200 volts, 30min) neutral.

EXAMPLE 56

$^{99m}$Tc complex of N[2-(((-methyl-2-allylthio) propionyl)amino)ethyl]-2-aminothiopenol N[2-(((2-methyl-2-allylthio)propionyl)amino) ethyl]-2-aminothiophenol, Example 34, was reacted with $^{99m}$Tc sodium pertechnetate by the method described in Example 49. TLC (50% ethyl acetate/hexane) R$_f$ 0.68, radiochemical purity 88%. HPLC (Radial-Pak C18, 70% acetonitrile/water, 2.0 ml/min R$_t$ 4.7 min, radiochemical purity 95%. Electrophoresis (0.1M NaH$_2$PO$_4$, pH 6.8, 200 volts, 30 min) neutral.

EXAMPLE 58

$^{99m}$Tc complex of N[2-(((2-methyl-2-(2-propynylthio)) propionyl)amino)ethyl]-2-(4-methoxybenzylthio)aniline N[2-(((2-methyl-2-(2-propynylthio))propionyl) amino) ethyl]-2-(4-methoxybenzyl-thio)aniline, Example 36, was reacted with $^{99m}$Tc sodium pertechnetate by the method described in Example 49. The crude complex was purified by HPLC (Nova-Pak C18, 50% ethanol/water, 2.0 ml/min. TLC (50% ethyl acetate/hexane) R$_f$ 0.51, radiochemical purity 88%.

EXAMPLE 58

$^{99m}$Tc complex of N[2-(((2-methyl-2-(2-hydroxyethylthio)) propionyl)amino) ethyl]-2-(4-methoxybenzylthio) aniline N[2-(((2-methyl-2-(2-hydroxyethylthio)) propionyl) amino)ethyl]-2-(4-methoxy benzylthio)aniline, Example 39, was reacted with $^{99m}$Tc sodium pertechnetate by the method described in Example 50. The mixture was heated at 60° C. for 30 minutes, and then purified by HPLC (Radial-Pak C18) R$_t$ 4.02 min, radiochemical purity 85%. TLC (50% ethyl acetate/hexane) R$_f$ 0.55, radiochemical purity 91%. Electrophoresis (0.1M NaH$_2$PO$_4$, pH 6.8, 200 volts, 30 min) neutral.

EXAMPLE 59

$^{99m}$Tc complex of N[2-(((2-methyl-2-(methoxycarbonyl methylene thio))propionyl) amino)ethyl]-2-(4-methoxybenzylthio)aniline N[2-(((2-methyl-2-(methoxycarbonyl methylene thio)) propionyl)amino)ethyl]-2-(4-methoxybenzylthio) aniline, Example 40, was reacted with $^{99m}$Tc sodium pertechnetate by the method described in Example 49. The crude complex was purified by HPLC (Nova-Pak C18, 50% ethanol/water, 1.5 ml/min) R$_t$ 9.33 min, radiochemical purity 95%. TLC (50% ethyl acetate/hexane) R$_f$ 0.10, radiochemical purity 97%. Electrophoresis (0.05M NaH$_2$PO$_4$, pH 4.5, 300 volts, 35 min) neutral.

EXAMPLE 60

$^{99m}$Tc complex of N[2-(((2-methyl-2-(3-aminopropylthio)) propionyl)amino)ethyl]-2-(4-methoxybenzylthio) aniline N[2-(((2-methyl-2-(3-aminopropylthio)) propionyl) amino)ethyl]-2-(4-methoxybenzylthio) aniline, Example 41, was reacted with $^{99m}$Tc sodium pertechnetate by the method described in Example 50. TLC (86% ethyl acetate/10% methanol/3% water/1% 15M ammonium hydroxide) R$_f$ 0.4, radiochemical purity 86%. HPLC (Nova-Pak C18, 50% acetonitrile/water, 2.0 ml/min) R$_t$ 4.39 min, radiochemical purity 68%.

EXAMPLE 61

$^{99m}$Tc complex of N[2-oxo-2(N$^1$((2-methyl-2-mercapto) propyl)amino)ethyl]-2-methylthioaniline N[2-oxo-2(N1((2-methyl-2-mercapto)propyl) amino) ethyl]-2-methylthioaniline, Example 46, was reacted with $^{99m}$Tc sodium pertechnetate by the method described in Example 50, without heating. The crude product was filtered through a Millex FG filter. TLC (50% ethyl acetate/hexane) R$_f$ 0.5, radiochemical purity 92%. HPLC (Nova-Pak C18, 70% acetonitrile/water, 2.0 ml/min) R$_t$ 3.56 min, radiochemical purity 98%. Electrophoresis (0.05M NaH$_2$PO$_4$, pH 4.5, 300 volts, 30 min) neutral.

EXAMPLE 62

$^{99m}$Tc complex of N[2-(((2-methyl-2-(2-chloroethylthio)) propionyl)amino) ethyl]-2-(4-methoxybenzylthio)aniline N[2-(((2-methyl-2-(2-chloroethylthio)) propionyl)amino) ethyl]-2-(4-methoxy-benzylthio)aniline, Example 47, was reacted with $^{99m}$Tc sodium pertechnetate by the method described in Example 49. The crude product was purified by HPLC (Nova-Pak C18, 60% ethanol/water, 1.5 ml/min) R$_t$ 3.50 min radiochemical purity 89%. TLC (ethyl acetate/hexane) R$_f$ 0.5, radiochemical purity 90%. Electro-phoresis (0.05M. NaH$_2$PO$_4$, pH 4.5, 300 volts, 30 min) neutral.

EXAMPLE 63

$^{99m}$Tc complex of N[2-(((2-methyl-2-(2-cyanoethylthio)) propionyl)amino)ethyl]-2-(4-methoxybenzylthio)aniline N[2-(((2-methyl-2-(2-cyanoethylthio)) propionyl)amino) ethyl]-2-(4-methoxybenzylthio)aniline, Example 48, was reacted with $^{99m}$Tc sodium pertechnetate by the method described in Example 49. The crude product was purified by HPLC (Nova-Pak C18, 60% ethanol/water, 1.5 ml/min) R$_t$ 3.89 min, radiochemical purity 89%. TLC (50% ethyl acetate/hexane) R$_f$ 0.30, radiochemical purity 83%. Electrophoresis (0.05M NaH$_2$PO$_4$, pH 4.5, 300 volts, 30 min) neutral.

EXAMPLE 64

BIOLOGICAL EVALUATION OF $^{99m}$Tc COMPLEXES

Distribution of the $^{99m}$Tc labelled compounds was evaluated in rats. Female Sprague-Dawley rats weighing 140 to 220 g (average 170 g) were anaesthetised with sodium pentobarbital and were injected in a tail vein with 0.05 to 10mCi of the $^{99m}$Tc labelled complex in a volume of 0.2 to 0.5 ml. At least two rats were injected for each time point.

The animals were sacrificed at 5 and 30 minutes post injection and selected organs were removed; the tails were discarded to avoid interference from the injection site. The radioactivity in each organ was measured at a standard geometry with a thallium iodide-activated sodium iodide scintillation counter adjusted for the 140 KeV emission of $^{99m}$Tc. The organs were also weighed to one hundredth of a gram and the activity was calculated as a percent of administered dose per gram. The results are reported in the following table. The important determinations are the amount of activity in the brain and the brain:blood ratio.

TABLE I

| Tc BRAIN BIOASSAY DATA | | | | | |
|---|---|---|---|---|---|
| Complexes | Time min. | Brain % dose | Brain: blood | Heart % dose | Heart: blood |
| T711 | 5 | 2.33 | 4.24 | 0.88 | 3.38 |
|  | 30 | 0.47 | 1.54 | 0.23 | 1.51 |
| T712 | 5 | 1.69 | 1.04 | 0.61 | 1.07 |
|  | 30 | 1.73 | 1.13 | 0.53 | 0.74 |
| T713 | 5 | 1.55 | 4.34 | 0.59 | 3.68 |
|  | 30 | 0.46 | 1.83 | 0.19 | 1.84 |
| T714 | 5 | 1.43 | 3.11 | 0.82 | 3.67 |
|  | 30 | 0.50 | 1.66 | 0.27 | 1.79 |
| T715 | 5 | 2.55 | 5.19 | 0.84 | 3.73 |
|  | 30 | 0.51 | 1.36 | 0.23 | 1.40 |
| T717 | 5 | 1.27 | 1.21 | 0.98 | 1.88 |
|  | 30 | 1.24 | 1.23 | 0.48 | 1.00 |
| T719 | 5 | 1.86 | 1.32 | 0.78 | 1.36 |
|  | 30 | 0.48 | 0.26 | 0.40 | 0.55 |
| T721 | 5 | 1.82 | 1.23 | 0.75 | 1.16 |
|  | 30 | 0.30 | 0.21 | 0.36 | 0.49 |
| T722 | 5 | 1.58 | 0.57 | 0.74 | 0.67 |
|  | 30 | 0.68 | 0.31 | 0.48 | 0.52 |
| T726 | 5 | 1.11 | 1.82 | 0.73 | 3.22 |
|  | 30 | 0.32 | 0.93 | 0.28 | 2.08 |

TABLE I-continued

Tc BRAIN BIOASSAY DATA

| Complexes | Time min. | Brain % dose | Brain: blood | Heart % dose | Heart: blood |
| --- | --- | --- | --- | --- | --- |
| T727 | 5 | 0.09 | 0.09 | 0.45 | 1.26 |
|  | 30 | 0.07 | 0.06 | 0.18 | 0.42 |
| T728 | 5 | 0.03 | 0.04 | 1.68 | 4.36 |
|  | 30 | 0.03 | 0.05 | 0.74 | 2.11 |
| T729 | 5 | 0.87 | 0.19 | 0.70 | 0.34 |
|  | 30 | 0.21 | 0.08 | 0.28 | 0.36 |
| T730 | 5 | 2.45 | 6.1 | 0.71 | 3.97 |
|  | 30 | 0.73 | 1.8 | 0.29 | 1.53 |
| T731 | 5 | 1.49 | 0.42 | 1.01 | 0.68 |
|  | 30 | 0.60 | 0.21 | 0.58 | 0.42 |

1. H F KUNG, M MOLNAR, J BILLINGS, R WICKS and M BLAU. J.Nucl.Med. 25 326 (1984).
2. H. F. KUNG. et al., 9th Int.Symp.Radiopharm. Chemistry, Paris, 6–10 Apr. 1992. Paper A11.
3. S. F. Taylor et al. J.Nucl.Med., 33, 1836 (1992).
4. N BRYSON, J C DEWAN, J LISTER-JAMES, A G JONES and A DAVISON, Inorg.Chem. 27 2154 (1988).
5. T. N. RAO et al. Nucl.Med.Biol., 19, 889 (1992).

We claim:

1. A neutral $^{99m}$Tc complex of the structure:

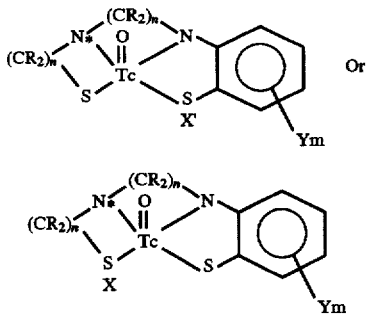

where
n is 2 or 3;
m is 0 to 4;
one $CR_2$ group adjacent the starred nitrogen atom represents CO and forms, together with the adjacent N atom, a —CONH—amide group, other groups R are the same or different at different places in the molecule, and each is H or $C_1$ to $C_6$ alkyl;

Y is the same or different at different places in the molecule and each is $C_1$–$C_4$ alkyl, alkoxyalkyl, alkoxy, amino, isothiocyanate or acyloxy;

each of X and X' is $C_1$–$C_6$ alkyl, alkenyl, alkynyl, hydroxyalkyl, alkoxyalkyl, aminoalkyl, carboxyalkyl, acyloxyalkyl, aminoalkyl, haloalkyl of nitriloalkyl.

2. The complex according to claim 1, wherein
n is 2;
m is 0;
R is H in all places except the $CR_2$ group which represents CO.

3. A brain imaging agent comprising a complex according to claim 1.

4. The complex according to claim 1, of structure:

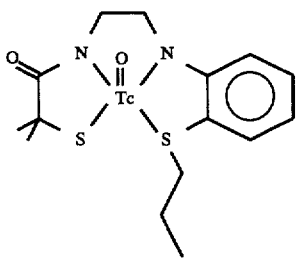

5. The complex according to claim 1, of structure:

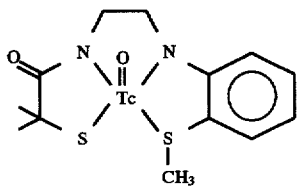

6. The complex according to claim 1, wherein Y is $C_1$–$C_4$ alkyl, alkoxyalkyl or alkoxy.

* * * * *